(12) United States Patent
Malek

(10) Patent No.: US 9,095,420 B2
(45) Date of Patent: Aug. 4, 2015

(54) ENDOVASCULAR STENT

(75) Inventor: Adel M. Malek, Weston, MA (US)

(73) Assignee: TUFTS MEDICAL CENTER, INC., Boston, MA (US)

( * ) Notice: Subject to any disclaimer, the term of this patent is extended or adjusted under 35 U.S.C. 154(b) by 58 days.

(21) Appl. No.: 13/981,396

(22) PCT Filed: Jan. 18, 2012

(86) PCT No.: PCT/US2012/021671
§ 371 (c)(1),
(2), (4) Date: Oct. 11, 2013

(87) PCT Pub. No.: WO2012/102919
PCT Pub. Date: Aug. 2, 2012

(65) Prior Publication Data
US 2014/0031920 A1   Jan. 30, 2014

Related U.S. Application Data

(60) Provisional application No. 61/435,592, filed on Jan. 24, 2011.

(51) Int. Cl.
A61F 2/06 (2013.01)
A61F 2/86 (2013.01)
A61F 2/88 (2006.01)
A61F 2/89 (2013.01)
A61F 2/852 (2013.01)
A61F 2/82 (2013.01)

(52) U.S. Cl.
CPC ... *A61F 2/06* (2013.01); *A61F 2/86* (2013.01); *A61F 2/88* (2013.01); *A61F 2/89* (2013.01); *A61F 2/852* (2013.01); *A61F 2002/067* (2013.01); *A61F 2002/068* (2013.01); *A61F 2002/823* (2013.01)

(58) Field of Classification Search
CPC .................................... A61F 2/06; A61F 2/08
USPC ................................................ 623/1.1–1.48
See application file for complete search history.

(56) References Cited

U.S. PATENT DOCUMENTS

| | | | |
|---|---|---|---|
| 6,190,402 B1 * | 2/2001 | Horton et al. | 623/1.11 |
| 7,740,791 B2 * | 6/2010 | Kleine et al. | 264/482 |
| 8,021,415 B2 * | 9/2011 | Houston et al. | 623/1.22 |
| 8,663,304 B2 * | 3/2014 | Wallace et al. | 623/1.12 |
| 2003/0109917 A1 | 6/2003 | Rudin et al. | |
| 2004/0055606 A1 * | 3/2004 | Hendricksen et al. | 128/207.14 |
| 2007/0021816 A1 | 1/2007 | Rudin | |
| 2008/0269871 A1 | 10/2008 | Eli | |
| 2008/0312733 A1 | 12/2008 | Jordan | |
| 2009/0069880 A1 * | 3/2009 | Vonderwalde et al. | 623/1.13 |
| 2010/0016950 A1 | 1/2010 | Berglund et al. | |
| 2011/0160833 A1 * | 6/2011 | Gonzalez et al. | 623/1.11 |
| 2012/0316632 A1 * | 12/2012 | Gao | 623/1.2 |
| 2013/0110221 A1 * | 5/2013 | Campbell et al. | 623/1.2 |
| 2013/0116655 A1 * | 5/2013 | Bacino et al. | 604/509 |
| 2013/0211489 A1 * | 8/2013 | Makower et al. | 623/1.2 |
| 2014/0249614 A1 * | 9/2014 | Levi et al. | 623/1.11 |
| 2015/0088239 A1 * | 3/2015 | Ben-Muvhar et al. | 623/1.3 |

* cited by examiner

*Primary Examiner* — Suzette J Gherbi
(74) *Attorney, Agent, or Firm* — Occhiuti & Rohlicek LLP

(57) ABSTRACT

An intravascular stent is provided for treatment of an aneurysm in a vessel wall of a cranial blood vessel. The stent includes at least one a flow-shaping member including a flow-facing surface that protrudes from an inner surface of the stent and is configured to control at least one of the direction, velocity and secondary flow characteristics of the blood flow within the aneurysm.

31 Claims, 18 Drawing Sheets

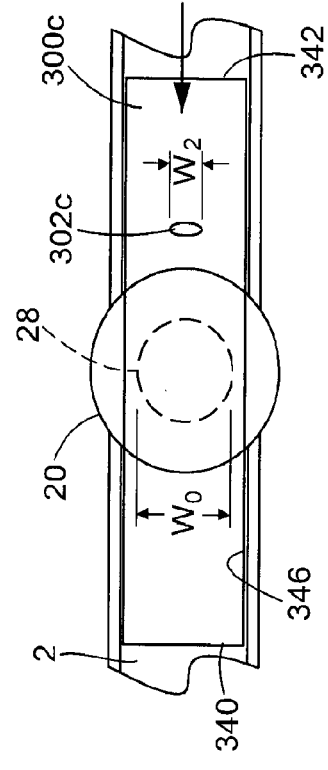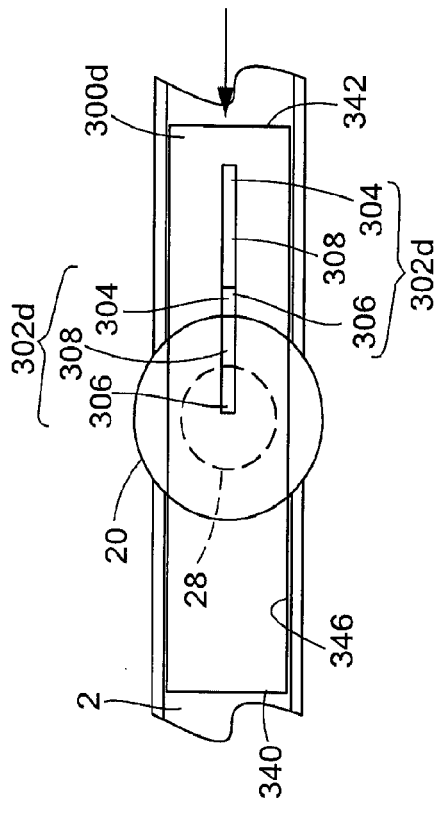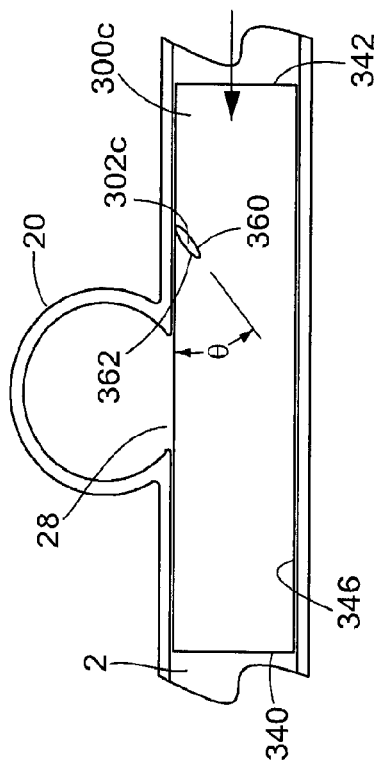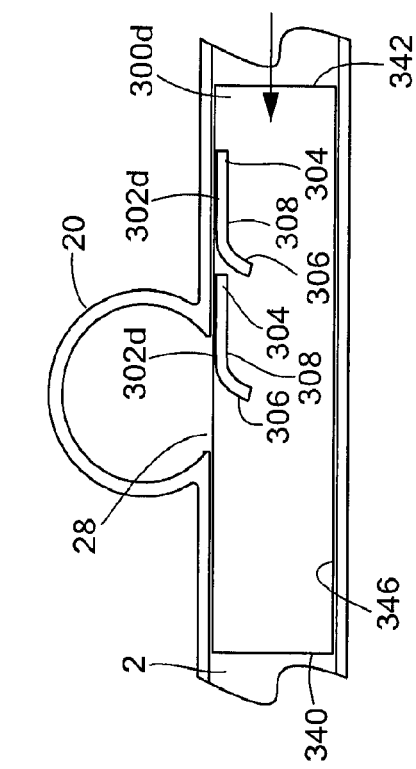
FIG. 10a
FIG. 10b
FIG. 11a
FIG. 11b

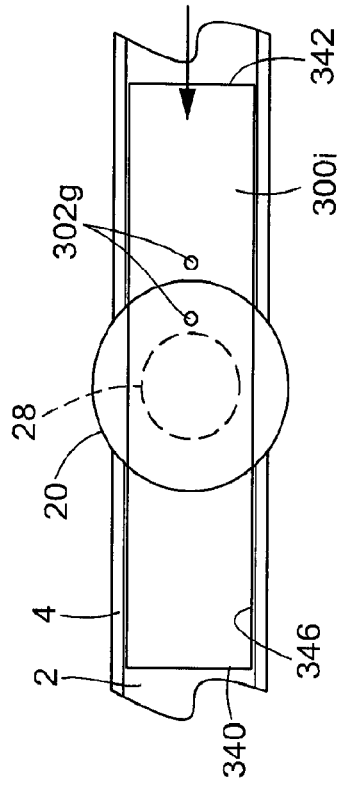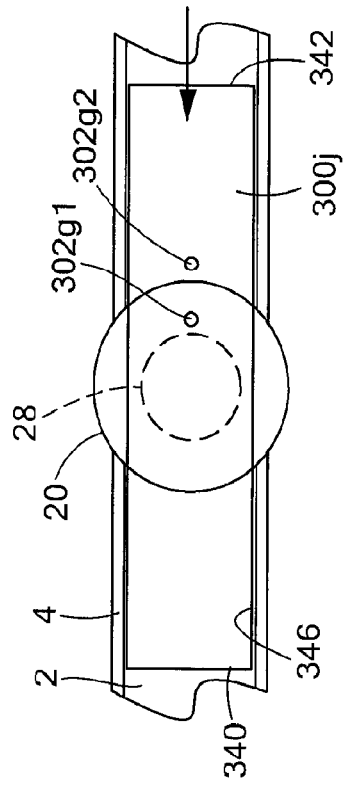
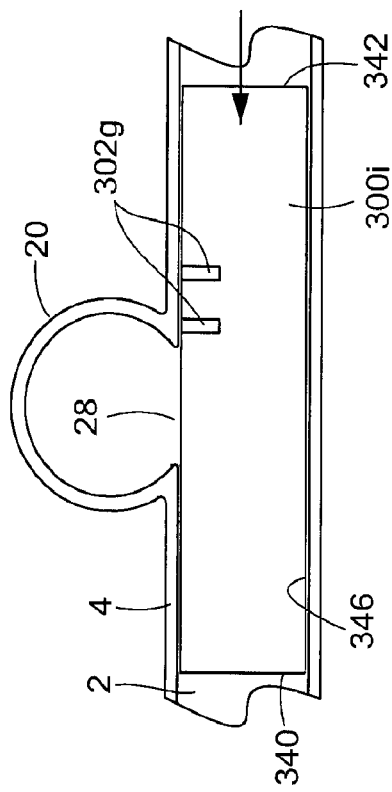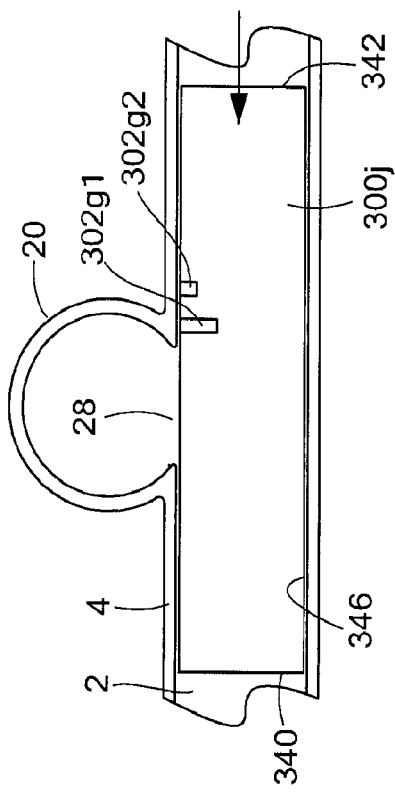
FIG. 16a   FIG. 17a
FIG. 16b   FIG. 17b

ENDOVASCULAR STENT

CROSS REFERENCE TO RELATED APPLICATIONS

This application is a National Stage of International Application No. PCT/US2012/021671 filed on Jan. 18, 2013, which claims priority to U.S. Provisional Application No. 61/435,592, filed Jan. 24, 2011, the contents of which are incorporated herein by reference in their entirety.

BACKGROUND OF THE INVENTION

A brain aneurysm, also called an intracranial aneurysm, is an abnormal bulge or ballooning in a blood vessel supplying the brain. The weakened area forms a sac that fills with blood. Intracranial aneurysms can rupture and cause bleeding into the brain. Usually this occurs in the area between the brain and the surrounding membrane (the arachnoid), called the subarachnoid space, causing a subarachnoid hemorrhage. Subarachnoid hemorrhage resulting from a ruptured intracranial aneurysm occurs approximately 35,000 times per year in the United States.

Currently, intracranial aneurysms are treated by microsurgical clipping or endovascular coiling. In the latter, the goal is to prevent aneurysm rupture by inserting a thin wire into the aneurysm forming a coiled structure which blocks blood flow into the aneurysm. In some treatment paradigms, intracranial stents are used within the blood vessel to buttress placement of coils. Such stents serve as a mechanical scaffold in order to help contain the coil mass within the aneurysm dome.

SUMMARY

In some aspects, an intravascular stent for treatment of an aneurysm in a vessel wall of a cranial blood vessel is provided. The aneurysm protrudes from, and defines an opening in, the vessel wall. The stent includes a flow-shaping member including a flow-facing surface that protrudes from an inner surface of the stent and is configured to control at least one of the direction, velocity and secondary flow characteristics of the blood flow within the aneurysm.

The stent may include one or more of the following features: The stent is configured to control blood flow both within the aneurysm and within the vessel in the vicinity of the aneurysm. The aneurysm has an inflow region adjacent a downstream side of the opening, where downstream is determined relative to a direction of blood flow within the vessel, and the stent is configured to control the blood flow within the aneurysm by directing blood flow away from the inflow region. The stent includes a series of axially spaced-apart annular struts in which adjacent struts are joined by axially extending links, and the flow-shaping surface is provided by a surface of at least one strut. The stent includes a single helically coiled strut, and the flow-shaping surface is provided by a surface of at least a portion of the strut. The stent includes a plurality of struts arranged to form a cylindrical body, and wherein the flow-shaping member comprises a vane protruding from an inner surface of the stent. The stent is configured to be disposed in the vessel so that the flow-shaping member extends at least partially across the opening while permitting substantially unobstructed blood flow into the aneurysm. The stent is configured to be disposed in the vessel so that the flow-shaping member is disposed in the vessel at a location upstream of the opening.

The stent may include one or more of the following additional features: The flow-shaping member protrudes inward from the inner surface of the stent so that the flow-facing surface extends in a non-normal direction relative to the inner surface of the stent. The flow-facing surface is disposed at an acute deflection angle that is measured relative to the inner surface of the stent. The deflection angle is in the range of 2 degrees to 60 degrees. The deflection angle is in the range of 3 degrees to 30 degrees. The deflection angle is in the range of 4 degrees to 15 degrees. The deflection angle of the flow-facing surface is configured to divert at least a portion of the blood flow toward an axial centerline of the stent. The deflection angle of the flow-facing surface is configured to divert at least a portion of the blood flow in a direction tangential to an axial centerline of the stent.

The stent may include one or more of the following additional features: The flow-shaping member has a generally elliptical cross section, the flow-shaping member being oriented so that the long axis of the elliptical cross section is angled relative to an inner surface of the stent. The flow-shaping member has a generally rectangular cross section, the flow-shaping member being oriented so that the long axis of the rectangular cross section is angled relative to an inner surface of the stent. The stent includes two vanes, the vanes being elongated and each including a first portion aligned with an axial direction of the vessel, and a second portion angled relative to the first portion. The second portion extends in a circumferential direction of the stent. The second portion extends in a radial direction of the stent. The two vanes are arranged so that a second portion of the first strut is disposed within the opening, and the second portion of the second strut overlies the first portion of the first strut. The two vanes are arranged so that the respective first portions are parallel to an axial direction of the strut, and the respective second portions are diverging.

The stent may include one or more of the following additional features: The flow-facing surface of each annular strut is disposed at an acute deflection angle that is measured relative to the inner surface of the stent. The deflection angle varies about a circumference of an annular strut. A first portion of one of the annular struts has a first deflection angle, a second portion of the one of the annular struts has a second deflection angle, and the first deflection angle is different from the second deflection angle. The first deflection angle is orthogonal to the second deflection angle. The first deflection angle is an acute angle, and the second deflection angle is zero. The first and second portions arc diametrically opposed.

The stent may include one or more of the following additional features: The flow-facing surface is configured to direct flow in a first direction, and the stent further comprises a second flow-shaping member including a second flow-facing surface configured to direct flow in a second direction that is different from the first direction. The flow-shaping members have the same shape. The flow-shaping members have different shapes. The first direction is orthogonal to the second direction. The first direction includes a flow-direction component in a first axial direction of the stent, and the second direction includes a flow-direction component in a direction opposed to the first axial direction of the stent. The stent includes a strut having a generally elliptical cross section, the long axis of the elliptical cross section being angled relative to a longitudinal axis of the stent so that the strut protrudes into the flow, the strut extending axially along a helical path, the helical path having a helix angle of greater than 60 degrees.

In some aspects, an intravascular stent is provided that is configured to modify vascular blood flow. The stent includes a vane including a flow-facing surface that protrudes from an inner surface of the stent and is configured to disrupt laminar blood flow within the stent.

The intracranial stent disclosed herein includes struts having a shape, orientation and thickness that advantageously impart changes to the blood flow characteristics within the aneurysm, within the stent, and/or within the blood vessel in the vicinity of the stent. By doing so, it is possible to shield the aneurysm from the various hemodyamic forces which can lead to its growth or rupture. Such changes may include one or more of blood flow velocity, direction and secondary blood flow characteristics including laminarity of blood flow. This is in contrast to some conventional stents in which stent struts are relied on as non-obstructive scaffolding within the vascular lumen.

Among other advantages, the intracranial stent locally alters one or more of the blood flow velocity, direction and/or secondary flow characteristics such as laminarity of flow. As a result blood flow and vessel wall shear forces are controlled within one or both of the aneurysm and the vessel in the vicinity of the aneurysm. Use of a stent to deliberately cause disruption of blood flow is clearly unconventional, since some blood flow disruptions, for example greater disruptions than those introduced by the disclosed stent, are associated with stenosis and thrombosis. To avoid these effects, some conventional stents such as intracoronary stents are designed to minimize disturbance of blood flow within the vessel, and to promote laminar blood flow.

Modes for carrying out the present invention are explained below by reference to an embodiment of the present invention shown in the attached drawings. The above-mentioned object, other objects, characteristics and advantages of the present invention will become apparent from the detailed description of the embodiment of the invention presented below in conjunction with the attached drawings.

BRIEF DESCRIPTION OF THE DRAWINGS

FIG. 3b is a schematic top sectional view of the stent of FIG. 3a.

FIG. 4b is a schematic top sectional view of the stent of FIG. 4a.

FIG. 5b is a schematic top sectional view of the stent of FIG. 5a.

FIG. 6b is a schematic top sectional view of the stent of FIG. 6a.

FIG. 7b is schematic side sectional view of the stent of FIG. 7a.

FIG. 8b is a schematic top sectional view of the stent of FIG. 8a.

FIG. 10a is schematic side sectional view of another alternative embodiment stent disposed within a blood vessel having a side wall aneurysm.

FIG. 10b is a schematic top sectional view of the stent of FIG. 10a.

FIG. 11a is schematic side sectional view of another alternative embodiment stent disposed within a blood vessel having a side wall aneurysm.

FIG. 11b is a schematic top sectional view of the stent of FIG. 11a.

FIG. 12b is a schematic top sectional view of the stent of FIG. 12a.

FIG. 13b is a schematic top sectional view of the stent of FIG. 13a.

FIG. 14b is a schematic top sectional view of the stent of FIG. 14a.

FIG. 15b is a schematic top sectional view of the stent of FIG. 15a.

FIG. 16a is schematic side sectional view of another alternative embodiment stent disposed within a blood vessel having a side wall aneurysm.

FIG. 16b is a schematic top sectional view of the stent of FIG. 16a.

FIG. 17a is schematic side sectional view of another alternative embodiment stent disposed within a blood vessel having a side wall aneurysm.

FIG. 17b is a schematic top sectional view of the stent of FIG. 17a.

FIG. 18b is a schematic top sectional view of the stent of FIG. 18a.

FIG. 19b is a schematic top sectional view of the stent of FIG. 19a.

FIG. 26 is a perspective view of the blood vessel of FIG. 22 illustrating calculated wall shear stress for an aneurysm treated with the stent of FIG. 2a.

DETAILED DESCRIPTION

Figure 1:
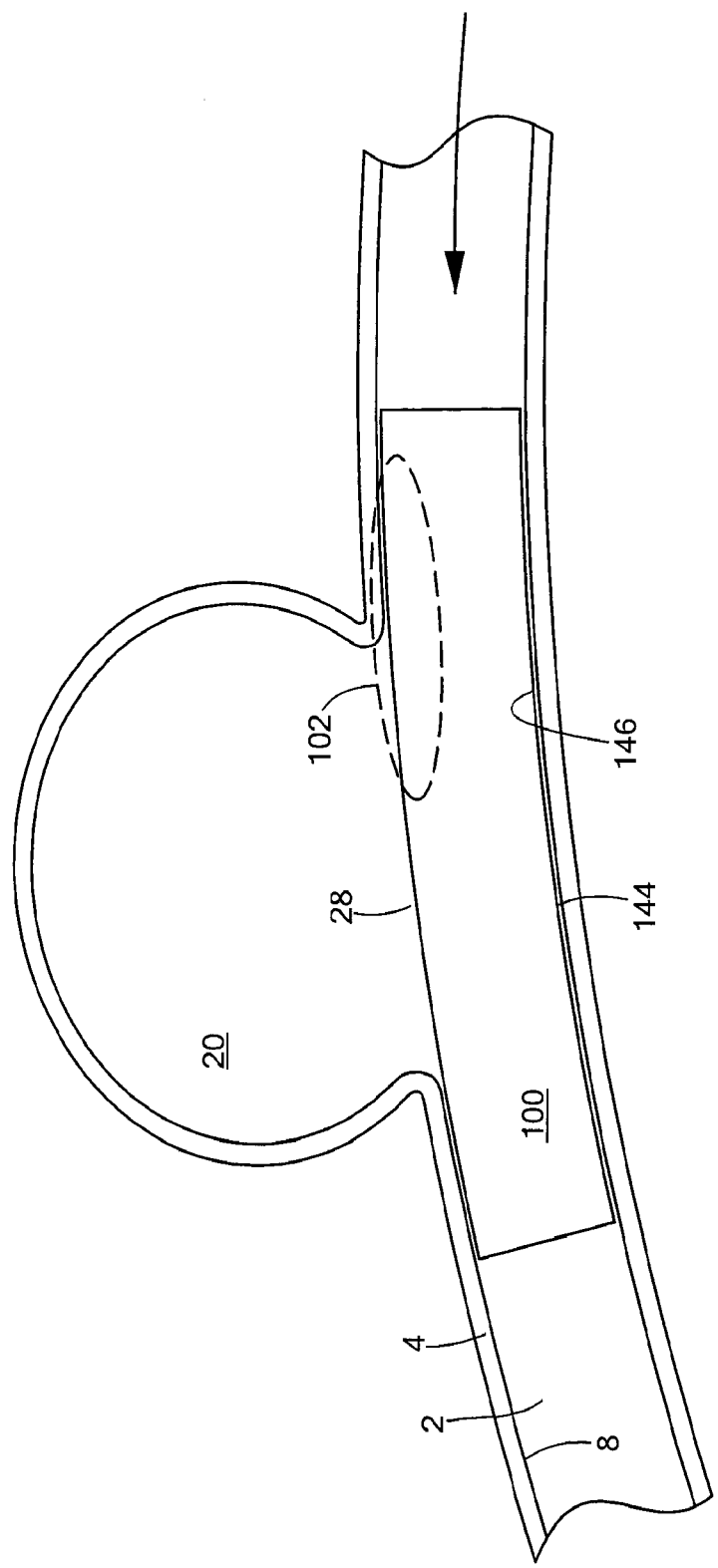
FIG. 1 is a schematic side sectional view of a stent disposed within a blood vessel having a side wall aneurysm, the stent including a flow-shaping member.

Referring to FIG. 1, a stent 100 is disposed within a blood vessel 2 that includes a sidewall aneurysm 20. As used herein, the term "sidewall aneurysm" refers to a type of aneurysm in which the blood vessel 2 forms an outward bulge from one portion of the vessel sidewall 4, defining an aneurysm opening 28 in the vessel sidewall 4. The stent 100 is placed within the blood vessel lumen 8 so as extend across the aneurysm opening 28.

In general and as will be discussed, the stent 100 includes internal blood flow-shaping members 102 (represented schematically in FIG. 1) that modify and direct blood flow within the blood vessel 2 in the vicinity of the stent 100, within the stent 100, and/or within the aneurysm 20, as discussed further below. By doing so, the hemodynamics and vessel wall shear forces are controlled to induce desired characteristics that can useful for aneurysm treatment. For example, in some embodiments, the stent 100 includes flow-shaping members 102 that may control the blood flow in such a way as to favor progression of thrombosis within the aneurysm 20. In other embodiments, the stent 100 may include flow-shaping members 102 that may control the blood flow to generate a different effect, such as altering blood flow velocity and or direction within the aneurysm 20, whereby vessel wall shear forces within the aneurysm 20 are reduced. In yet other embodiments, the stent 100 may include flow-shaping members 102 that may control the blood flow to generate a still different effect, such as altering blood flow velocity and or direction in a portion of the blood vessel 2 upstream from the aneurysm 20 relative to the blood flow direction whereby shear forces within the aneurysm 20 are reduced. In the figures, the blood flow direction within the vessel 2 is indicated by an arrow. Throughout the following description, the terms "upstream" and "downstream" are made with reference to the direction of blood flow within the vessel 2.

Figure 2A:
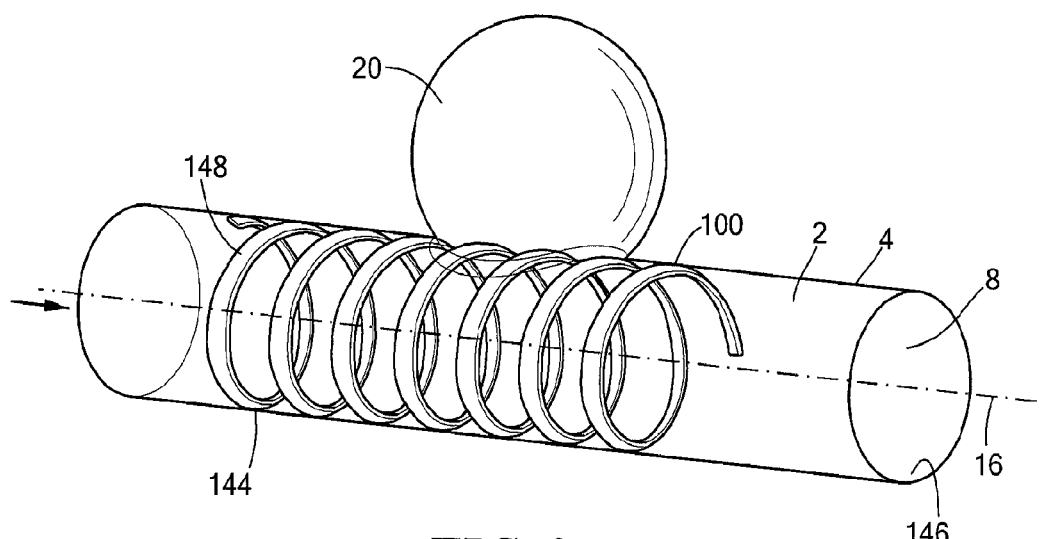
FIG. 2a is a perspective view of a stent formed of a helically wound strut disposed within a blood vessel having a side wall aneurysm.
Figure 2B:
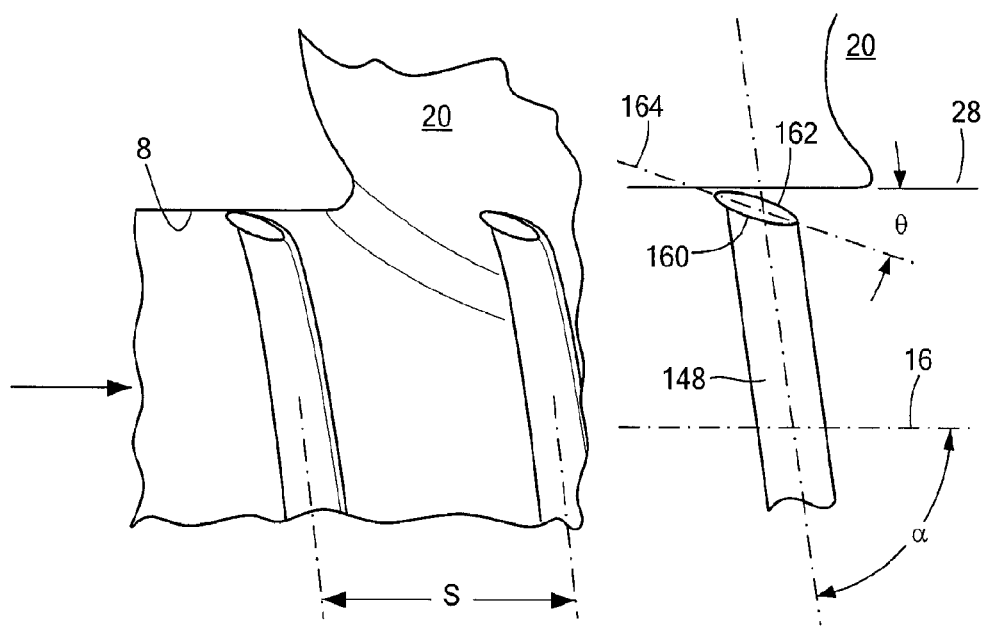
FIG. 2b is an enlarged view of a portion of the stent of FIG. 2.

Referring also to FIGS. 2a and 2b, stent 100 is a hollow cylindrical member having a stent outer surface 144 and a stent inner surface 146. The stent 100 may be self-expanding and may be implanted via a delivery catheter (not shown). The stent 100 is formed of a single coiled wire strut 148 formed of a metal filament that is wound into a helical shape, and which serves as a flow-shaping member, as discussed further below. In some embodiments, the strut 148 has a thickness in the range of 45 to 60 µm, and as such is thin relative to struts used to form non-intracranial stents, including for example cardiac stents. The relative thinness of the stent 100 is required to accommodate the relative delicacy of the intracranial blood vessels 2 in which they are deployed. For example, although when deployed stent 100 expands to correspond to the size of the vessel lumen 8, the stent 100 does not embed within the vessel walls 4 reflecting the relative thinness and fragility of the vessel walls. The stent 100 is polished to prevent unwanted areas of thrombosis and restenosis and may also be coated with a bio-degradable lubricious coating to facilitate deployment and decrease friction during use.

The coiled wire strut 148 of the stent 100 is formed having a large number of coil turns for a given stent length, whereby the helix angle $\alpha$, or angle of the strut 148 relative to an axial direction 16 of the blood vessel 2, is relatively large. For example, the helix angle $\alpha$ is desired to be at least 55 degrees. In the illustrated embodiment the helix angle $\alpha$ is about 83 degrees.

In addition the coiled wire strut 148 is provided with an elongated cross-section that includes a flow-facing surface 160 and a vessel facing surface 162 that is opposed to the flow-facing surface 160. The flow-facing and vessel facing surfaces 160, 162 are relatively long compared to the thickness of the strut 148 and are generally parallel to a long axis 164 of the strut cross section. In the illustrated embodiment, the cross sectional shape of the strut 148 is generally elliptical, such that it acts as a hydrofoil.

In order to direct blood flow away from the vessel wall 4, the strut 148 is arranged so that the cross-sectional long axis 164 of the strut 148 is oriented at a deflection angle $\theta$ relative to the inner surface 8 of the blood vessel 2. As a result, the strut 148 protrudes inward from vessel wall 4 so that the flow-facing surface 160 extends in a non-normal direction relative to vessel wall 4. In some embodiments, the deflection angle $\theta$ is in the range of 2 degrees to 60 degrees. In other embodiments, the deflection angle $\theta$ is in the range of 3 degrees to 30 degrees. In the illustrated embodiment, the deflection angle $\theta$ is about 25 degrees. Due to the angled configuration of the flow-facing surface 160 of the strut 148, blood flow direction is diverted so as to include at least a component directed in the radial direction of the stent 100, that is, toward an axial centerline of the stent 100. In addition, due to the helical configuration of the strut 148, blood flow direction is diverted so as to include another component directed in a circumferential (tangential) direction of the stent 100, that is, a rotational component about an axial centerline of the stent 100.

It should be noted that although the stent 100 is positioned in the vicinity of the aneurysm 20 so that portions of several turns of the coiled wire strut 148 extend across the aneurysm opening 28, sufficient spacing S is provided between adjacent turns of the strut 148 so that the stent 100 does not act as a barrier preventing flow into the aneurysm 20. Rather, the strut 148 deflects a portion of the blood flow away from the aneurysm opening 28, while permitting blood flow through the aneurysm opening 28 in a directed manner.

Although the cross sectional shape of the strut 148 of the stent 100 is disclosed as being generally elliptical, the strut is not limited to this shape. For example, the strut 148 may have other cross sectional shapes, including, but not limited to circular, rectangular, or tear-drop.

Although in the illustrated embodiment, the deflection angle $\theta$ of the strut 148 of the stent 100 is uniform along the length of the strut 100, the deflection angle $\theta$ is not limited to being uniform. For example, the deflection angle $\theta$ can be non-uniform such that portions of the strut in adjacent turns can have different deflection angles $\theta$. Similarly, although in the illustrated embodiment, the helix angle α of the strut 148 of the stent 100 is uniform along the length of the strut 100, the helix angle a can vary along the length of the strut 100.

Referring to FIGS. 3-10, an alternative stent 200 also includes internal blood flow-shaping members that modify and direct blood flow within the blood vessel 2 in the vicinity of the stent 200, within the stent 200, and/or within the aneurysm 20. The stent 200 is a hollow cylindrical member formed of annular struts 248 arranged in series along an axial direction of the strut 200, in which adjacent struts 248 are mutually spaced apart and connected using axially extending links 250. Each annular strut 248 is formed of a metal filament that is arranged into a generally circular shape. Like the wire strut 148 of the previous embodiment, the strut 248 has a thickness in the range of 45 to 60 μm. The stent 200 is polished to prevent unwanted areas of thrombosis and restenosis and may also be coated with a bio-degradable lubricious coating to facilitate deployment and decrease friction during use.

At least one annular strut 248 serves as a flow-shaping member. Each annular strut 248 is provided with an elongated cross-section and includes a flow-facing surface 260 and a vessel facing surface 262 that is opposed to the flow-facing surface 260. The flow-facing and vessel facing surfaces 260, 262 are relatively long compared to the thickness of the strut 248, and are generally parallel to a long axis 264 of the strut cross section. In the illustrated embodiment, the cross sectional shape of the strut 248 is generally elliptical, such that it acts as a hydrofoil.

The stent 200 is positioned in the vicinity of the aneurysm 20 so that portions of two or more annular struts 248 extend across the aneurysm opening 28. Like the previous embodiment, sufficient spacing S is provided between adjacent annular struts 248 so that the stent 200 does not act as a barrier preventing flow into the aneurysm 20. Rather, the individual struts 248 each deflect a portion of the blood flow away from the aneurysm opening 28, while permitting blood flow through the aneurysm opening 28 in a directed manner.

In order to direct a portion of the blood flow away from the vessel wall 4, the long axis 264 of the strut 248 is oriented at a deflection angle θ relative to the inner surface 8 of the blood vessel 2.

Figure 3A:
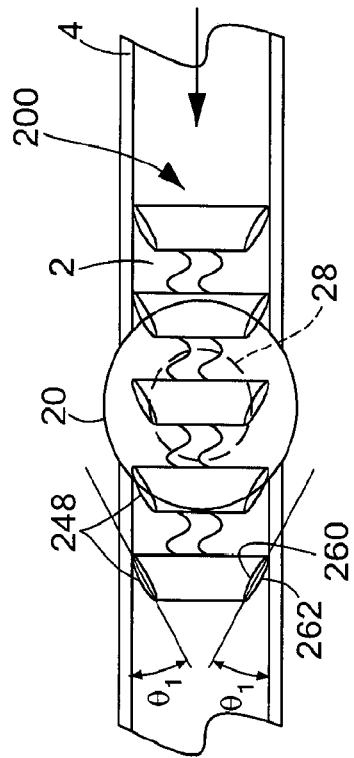
FIG. 3a is schematic side sectional view of an alternative embodiment stent formed of an annular strut disposed within a blood vessel having a side wall aneurysm.
Figure 3B:
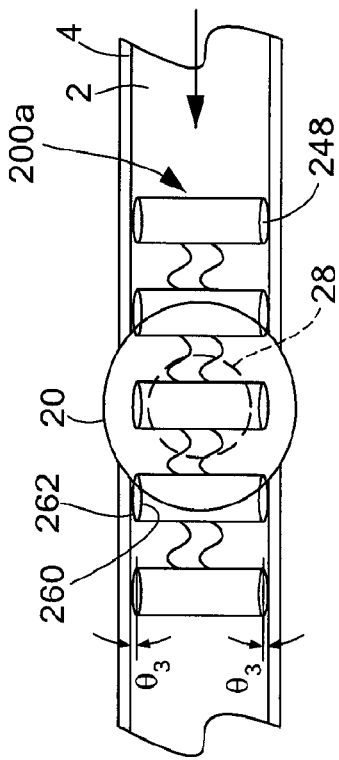

Referring particularly to FIGS. 3a and 3b, the stent 200 includes annular struts 248 that are each formed to have a uniform deflection angle θ1 about the circumference of the vessel 2, such that each strut 248 has the same deflection angle θ1 along a first side 34 of the vessel 2 corresponding to the aneurysm 20 and along a second side 36 of the vessel that is opposed to the first side 34.

Figure 4A:
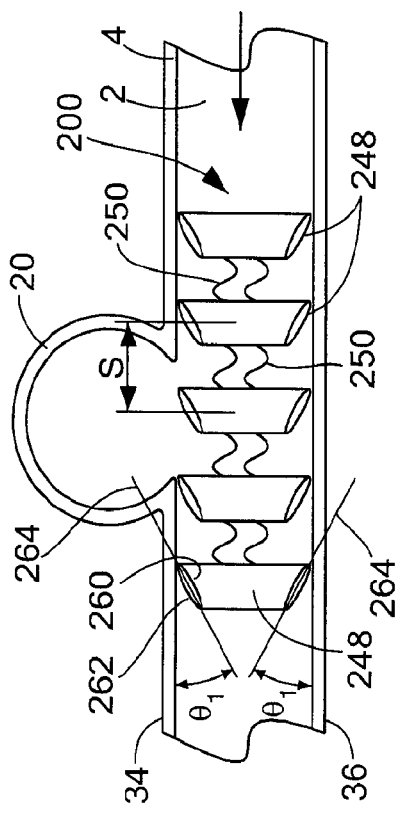
FIG. 4a is schematic side sectional view of another alternative embodiment stent formed of an annular strut disposed within a blood vessel having a side wall aneurysm.
Figure 4B:
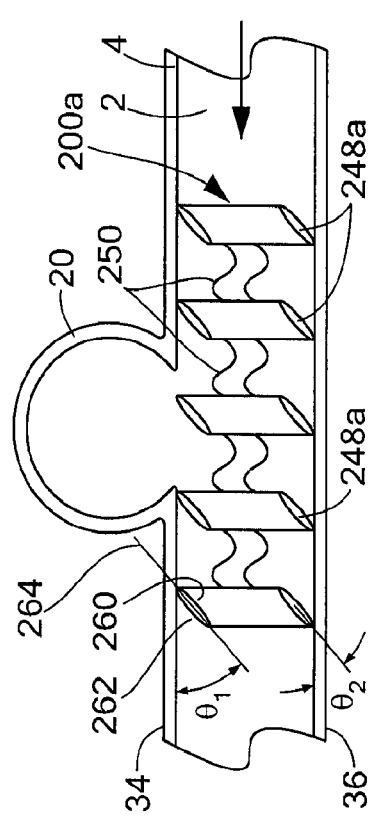

Referring to FIGS. 4a and 4b, a variation in annular strut configuration is illustrated with respect to a stent 200a that includes an annular strut 248a that is formed to have a first deflection angle θ1 along the first side 34 of the vessel 2, and a second deflection angle θ2 along the second side 36 of the vessel 2. For example, the first and second deflection angles θ1, θ2 may be generally equal in magnitude and have opposed directions.

Figure 5A:
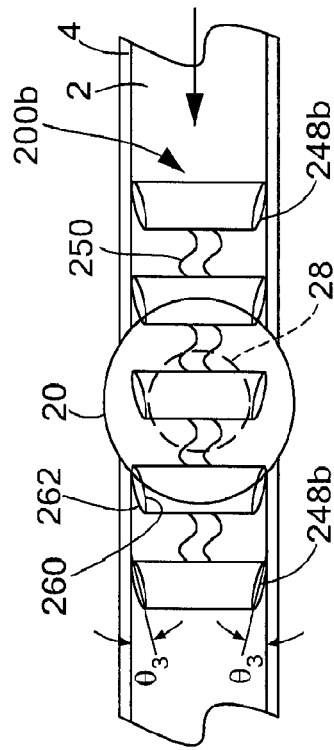
FIG. 5a is schematic side sectional view of another alternative embodiment stent formed of an annular strut disposed within a blood vessel having a side wall aneurysm.
Figure 5B:
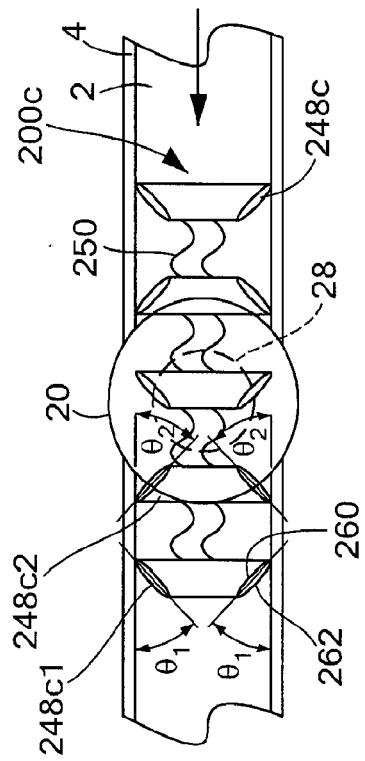

Referring to FIGS. 5a and 5b, another variation in annular strut configuration is illustrated with respect to a stent 200b that includes annular struts 248b that are formed to have a first deflection angle θ1 along the first side 34 of the vessel 2, and a second deflection angle θ2 along the second side 36 of the vessel. For example, in the illustrated embodiment, the first angle θ1 is acute, and the second angle θ2 is substantially zero. A shown in FIG. 5b, the deflection angle of the annular strut 248b smoothly transitions between T1 and T2, such that the deflection angle θ3 along a side of the vessel 2 between the first side 34 and second sides 36 is θ1<θ3<θ2.

Figure 6A:
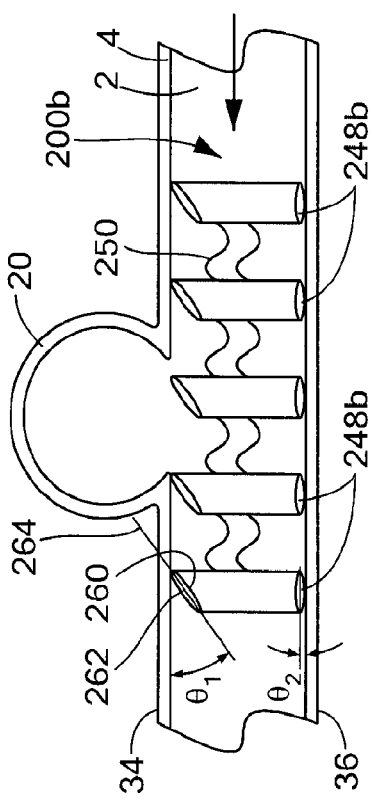
FIG. 6a is schematic side sectional view of another alternative embodiment stent formed of an annular strut disposed within a blood vessel having a side wall aneurysm.
Figure 6B:
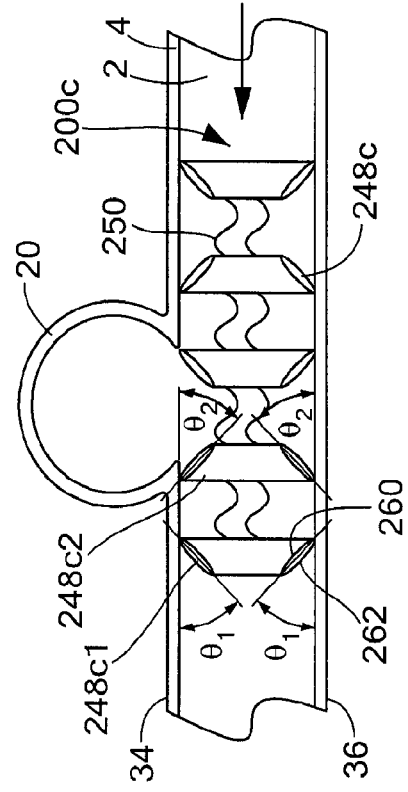

Referring to FIGS. 6a and 6b, still another variation in annular strut configuration is illustrated with respect to a stent 200c that includes annular struts 248c. Like the stent 200 shown in FIGS. 3 and 4, the stent 200c includes annular struts 248c that are formed to have a uniform angle θ1 about the circumference of the vessel 2. However, adjacent annular struts 248c1, 248c2 . . . are provided with different deflection angles. For example, in the illustrated embodiment, one strut 248c1 has first deflection angle θ1, and the adjacent strut 248c2 has a second deflection angle θ2. The second deflection angle θ2 may differ in magnitude and or direction from the first deflection angle θ1. In some embodiments, the first and second deflection angles θ1, θ2 may be mutually orthogonal.

In each of the stents 200, 200a, 200b, 200c, the annular strut 248 protrudes inward from vessel wall 4 so that the flow-facing surface 260 extends in a non-normal direction relative to vessel wall 4. In some embodiments, the deflection angle θ is in the range of 2 degrees to 60 degrees. In other embodiments, the deflection angle θ is in the range of 3 degrees to 30 degrees. In still other embodiments, the deflection angle θ is in the range of 4 degrees to 15 degrees. Due to the angled configuration of the flow-facing surface 260 of the strut 148, blood flow direction is diverted so as to include at least a component directed in the radial direction of the stent 200, that is, toward an axial centerline of the stent 200. In addition, due to the annular configuration of the strut 248, blood flow direction may also diverted so as to include another component directed in a circumferential (tangential) direction of the stent 200, that is, a rotational component about an axial centerline of the stent 200.

Figure 7A:
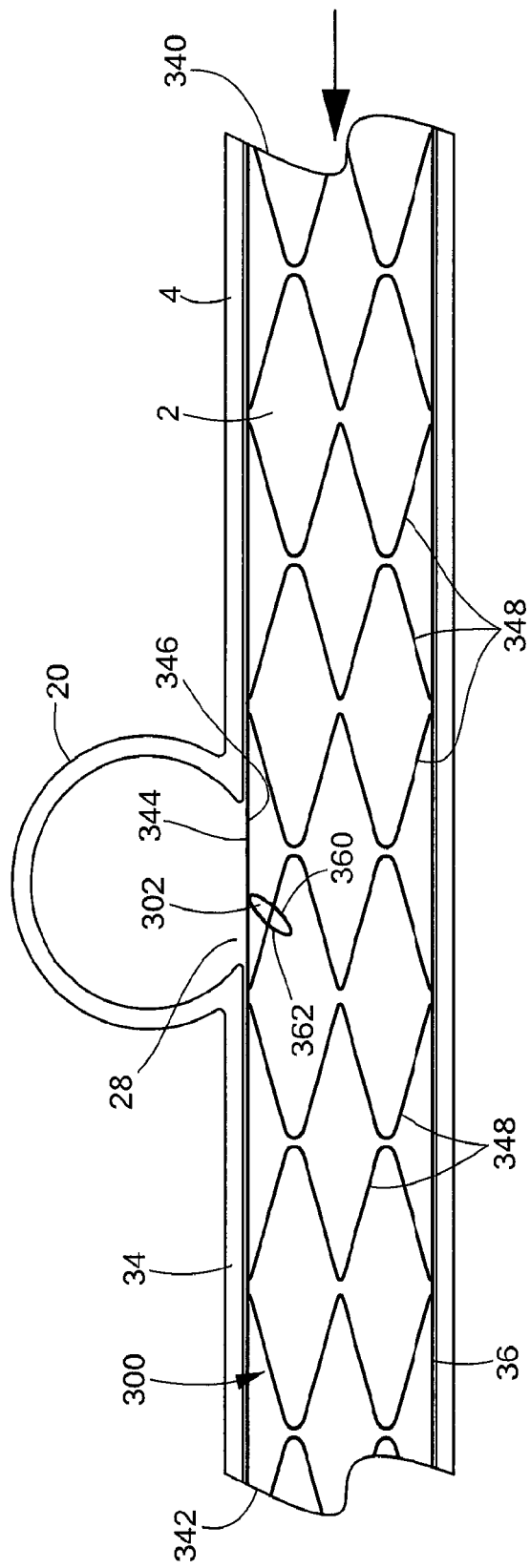
FIG. 7a is a side sectional view of a stent disposed within a blood vessel having a side wall aneurysm, the stent including an open cell strut structure and a vane protruding from an inner surface of the stent.
Figure 7B:
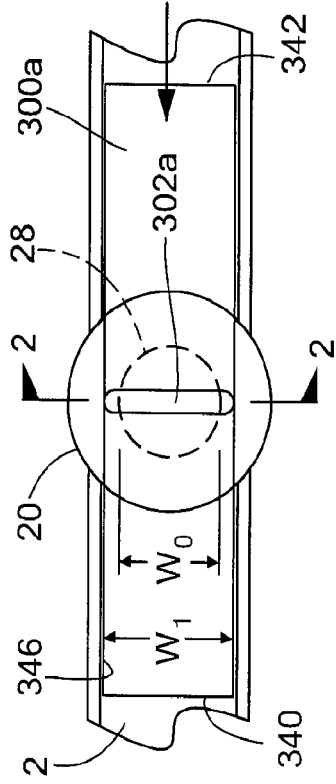
Figure 7C:
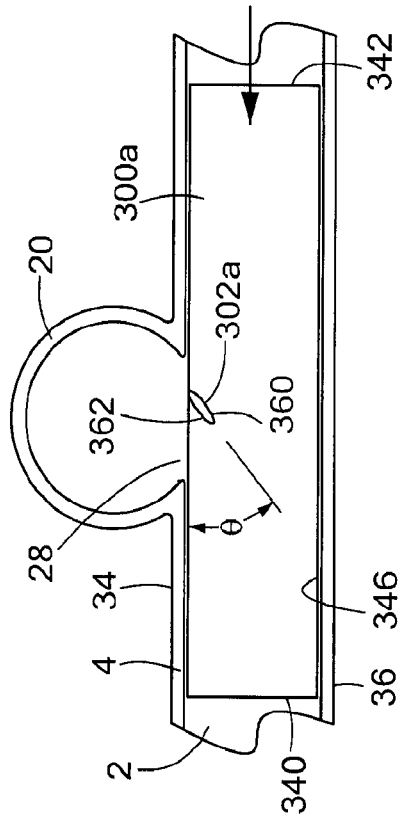
FIG. 7c is a schematic top sectional view of the stent of FIG. 7b.

Referring to FIG. 7a-7c, another alternative stent 300 includes internal blood flow-shaping members (shown schematically in FIG. 11 as 302) that modify and direct blood flow within the blood vessel 2 in the vicinity of the stent 300, within the stent 300, and/or within the aneurysm 20. The stent 300 is a hollow cylindrical member formed of thin metal filament struts 348 arranged in an open cell structure. Unlike previous embodiments in which the struts 148, 248 provided the flow-shaping member, the struts 348 of the stent 300 are minimally disruptive to blood flow, and instead merely provide a scaffold within the blood vessel 2 and a support structure to which at least one flow-shaping member 302 is mounted. The stent 300 has an open first end 340 corresponding to the flow inlet end, and a second end 342 opposed to the first end and corresponding to the flow outlet end. The stent 300 has an outer surface 344 and an inner surface 346, is polished to prevent unwanted areas of thrombosis and restenosis, and may also be coated with a bio-degradable lubricious coating to facilitate deployment and decrease friction during use.

Each flow-shaping member 302 includes a flow-facing surface 360, and a leeward surface 362 that is opposed to the flow-facing surface 360.

Referring to FIGS. 7a and 7b, the stent 300 includes a flow-shaping member 302 in the form of a vane 302a disposed generally midway between the stent first and second ends 340, 342. The vane 302a protrudes inward from an inner surface 346 of the stent 300. The vane 302a extends along a portion of the circumference of the stent 300. In the illustrated embodiment, the vane 302a is elongated in the circumferential direction such that it has a width w1 that is greater than the width wo of the aneurysm opening 28. The vane 302a protrudes inward from the stent inner surface 346 so that the flow-facing surface 360 extends in a non-normal direction, and defines a deflection angle θ relative to the stent inner surface 346. In the embodiment shown in FIGS. 12 and 13, the stent 300 is disposed in a blood vessel 2 so that the vane 302a is positioned at a location corresponding to the first side 34 of the vessel 2, and so that the vane 302a is disposed at a location corresponding to the aneurysm opening 28.

Figure 8A:
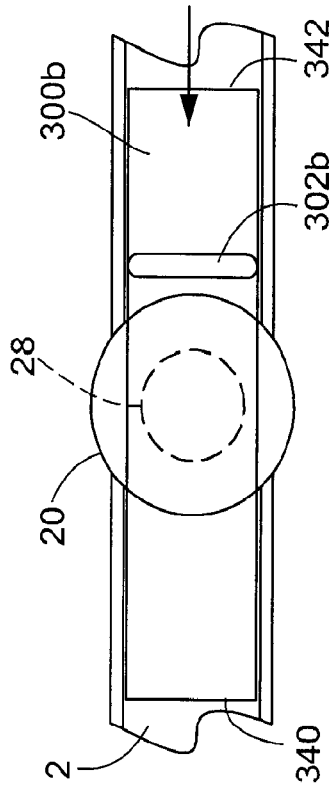
FIG. 8a is schematic side sectional view of an alternative embodiment stent disposed within a blood vessel having a side wall aneurysm.
Figure 8B:
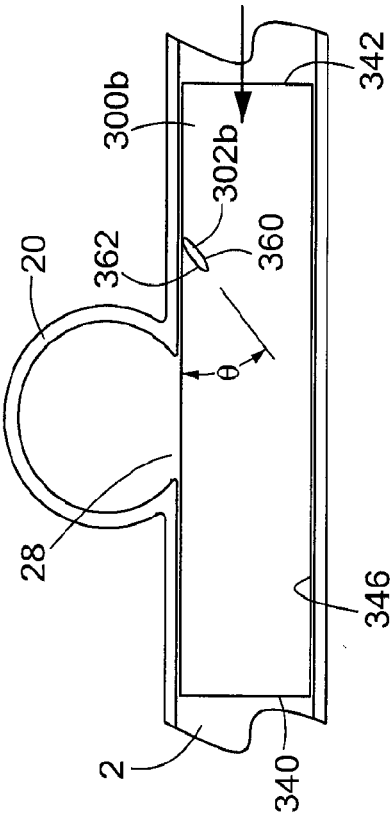

As seen in FIGS. 8a and 8b, a variation in vane position is illustrated with respect to a stent 300b that includes a vane 302b that is identical to the vane 302a except that it is not positioned at a location corresponding to the aneurysm opening 28. For example, the vane 302b is positioned upstream of the aneurysm opening 28.

Figure 9C:
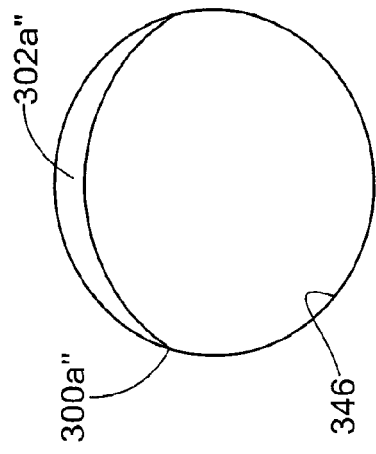
FIG. 9a-9f are transverse sectional views of the stent of FIG. 7c as seen along line 2-2 illustrating possible variations in vane profile.
Figure 9F:
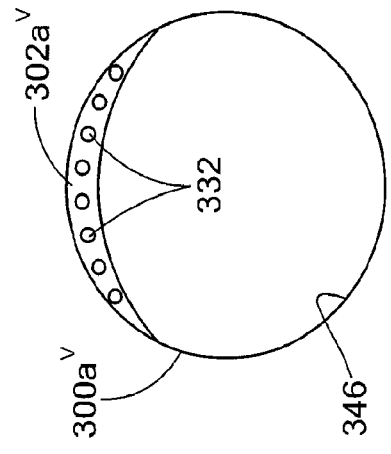
Figure 9B:
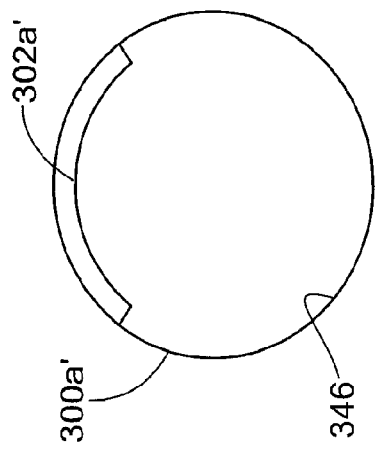
Figure 9E:
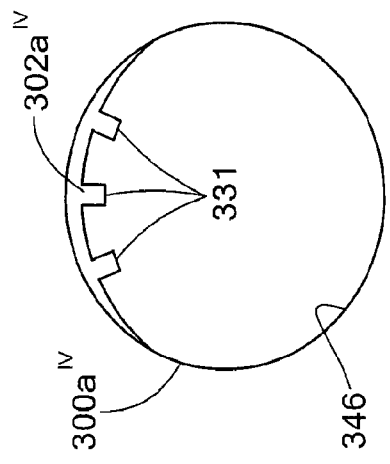
Figure 9A:
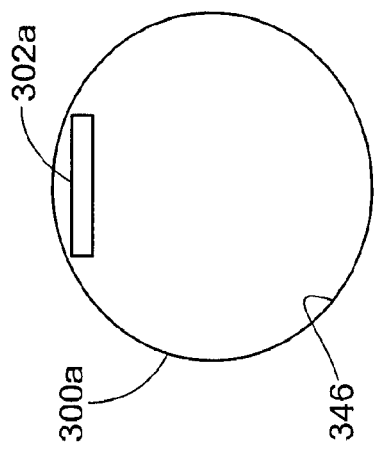
Figure 9D:
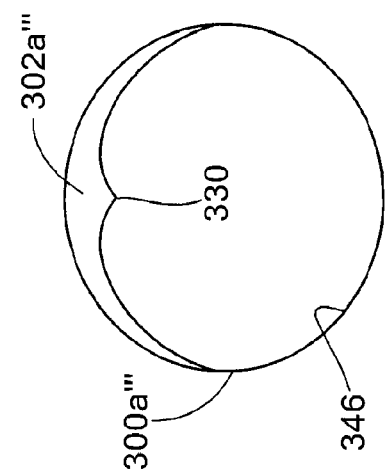

Referring to FIGS. 9a-9f, when viewed in the axial direction of the stent 300 the vanes 302a, 302b may have any appropriate profile required to achieve the desired blood flow characteristics. For example, the vane profile may be rectangular (FIG. 9a), or may be arcuate (FIGS. 9b-9f) so as to conform to the inner periphery of the stent 300. In addition, the vane ends may be formed to protrude stepwise from the stent inner surface 346 (FIGS. 9a and 9b) or may taper smoothly from the stent inner surface 346 (FIGS. 9c-9f). In some embodiments, the vane profile may be irregular so as to include one or more protrusions 330, 331 (FIGS. 9d-9e). In some embodiments the vane 302 may include perforations 332 (FIG. 9f).

As seen in FIGS. 10a and 10b, a variation in vane size is illustrated with respect to a stent 300c that includes a vane 302c that is identical to the vane 302b except that it is of a relatively short dimension in the in the circumferential direction. For example, the vane 302c is has a width w2 that is at most one half the width wo of the aneurysm opening 28.

Referring to FIGS. 11a-14b, examples of possible variations in vane shape are illustrated. The vane 302 may have any shape that is appropriate to achieve the desired blood flow characteristics. The following examples are non-limiting, and are presented to illustrate some of the possible vane shape variations that may be used to modify and direct blood flow within the blood vessel 2 in the vicinity of the stent 200, within the stent 200, and/or within the aneurysm 20.

Referring now to FIGS. 11a and 11b, a variation in vane shape is illustrated with respect to a stent 300d that includes a vane 302d that is an elongated, thin body that is arranged along the stent inner surface 346 so that an axial direction of the vane is aligned with the axial direction of the stent 300d. The vane includes a first end 304, a second end 306 disposed downstream relative to the first end 304, and a mid portion 308 disposed between the first and second ends 304, 306. The vane 302d is curved to form a generally ski-shape such that the first end 304 and mid portion 308 are contiguous with the stent inner surface 346, and such that the second end 306 curves away from the stent inner surface 346. In the illustrated embodiment, the second end 306 curves radially inward toward the axial centerline of the stent 300d. In some embodiments, the second end 306 is positioned at a location corresponding to the aneurysm opening 28, but the vane 300d is not limited to this position. In some embodiments, the stent 300d includes more than one vane 302d. For example, two vanes 302d may be provided that are arranged generally end-to-end along the axial direction of the stent 300d such that they are slightly overlapping along the axial direction of the stent 300d. In this embodiment, the blood flow within the stent 300d is redirected in a radially inward direction due to the shape and orientation of the second end 306 of the vane 302d.

Figure 12A:
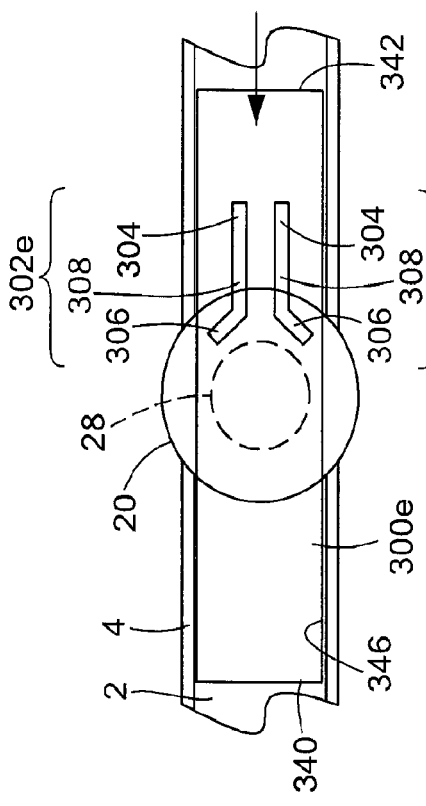
FIG. 12a is schematic side sectional view of another alternative embodiment stent disposed within a blood vessel having a side wall aneurysm.
Figure 12B:
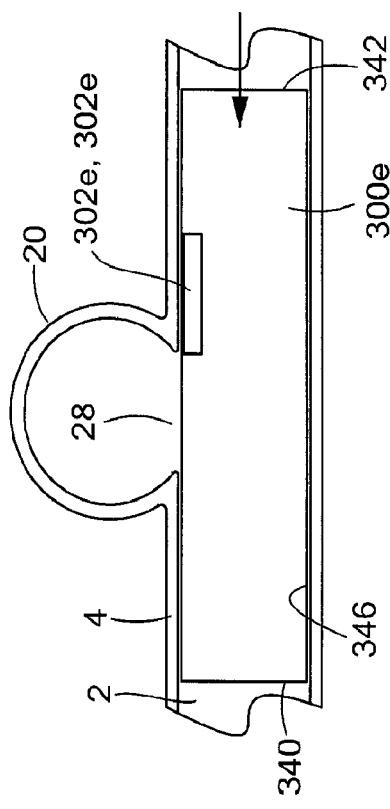

Referring to FIGS. 12a and 12b, another variation in vane shape is illustrated with respect to a stent 300e that includes a pair of vanes 302e that are identical to the vanes 302d of the preceding example, except that the vanes 302e are arranged side by side so as to be spaced apart along a circumferential direction of the stent 300e. In addition, the vanes 302e are oriented so that each of the first end 304, second end 306 and mid portion 308 are contiguous with the stent inner surface 346 such that the curved second end 306 extends along a circumferential direction of the stent 300e. In this embodiment, the curved second ends 306 are positioned closely adjacent to the aneurysm opening 28 on an upstream side of the aneurysm opening 28, and the blood flow within the stent 300e is redirected in a circumferential (tangential) direction due to the shape and orientation of the second end 306 of the vane 302e.

Figure 13A:
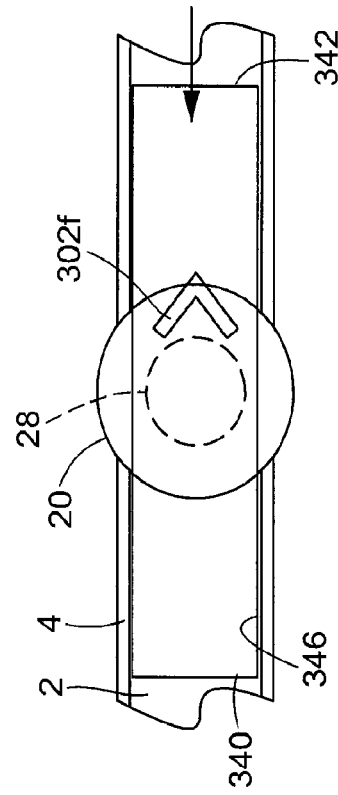
FIG. 13a is schematic side sectional view of another alternative embodiment stent disposed within a blood vessel having a side wall aneurysm.
Figure 13B:
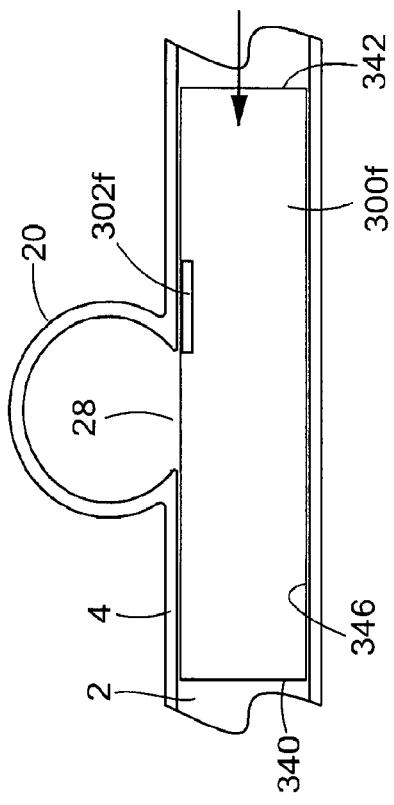

Referring to FIGS. 13a and 13b, another variation in vane shape is illustrated with respect to a stent 300f that includes a vane 302f that is generally V shaped. The vane 302f is oriented so that an apex 310 of the vane 302f is upstream relative to the diverging legs 312 of the vane 302f. In addition, the vane 302f may be positioned so that the diverging legs 302f surround a portion of the aneurysm opening 28 along an upstream side thereof. In this embodiment, the blood flow within the stent 300f is redirected in a circumferential (tangential) direction due to the diverging shape and orientation of the vane 302f.

Figure 14A:
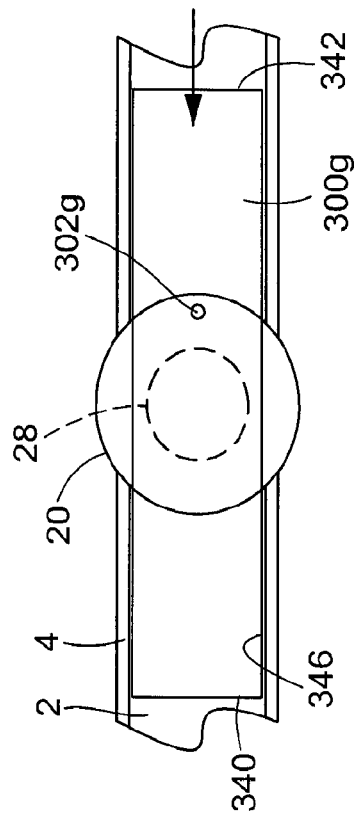
FIG. 14a is schematic side sectional view of another alternative embodiment stent disposed within a blood vessel having a side wall aneurysm.
Figure 14B:
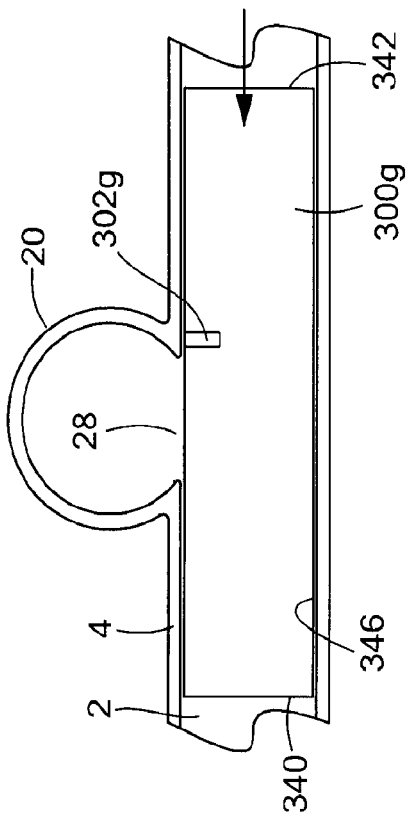

Referring to FIGS. 14a and 14b, another variation in vane shape is illustrated with respect to a stent 300g that includes a vane 302g that is generally rod shaped. The vane 302g is oriented so that it protrudes generally radially inward from the stent inner surface 346 at a location adjacent to the aneurysm opening 28 on an upstream side thereof.

Referring to FIGS. 15a-19b, examples of possible variations in vane configuration are illustrated. For illustration purposes, the examples are presented with reference to the rod-shaped vane 302g, but one of ordinary skill will understand that vane configuration variations are not limited to the rod-shaped vane 302g. Rather, the flow-shaping member 302 may be placed in any configuration that is appropriate to achieve the desired blood flow characteristics. The following examples are non-limiting, and are presented to illustrate some of the possible vane variations that may be used to modify and direct blood flow within the blood vessel 2 in the vicinity of the stent 200, within the stent 200, and/or within the aneurysm 20.

Figure 15A:
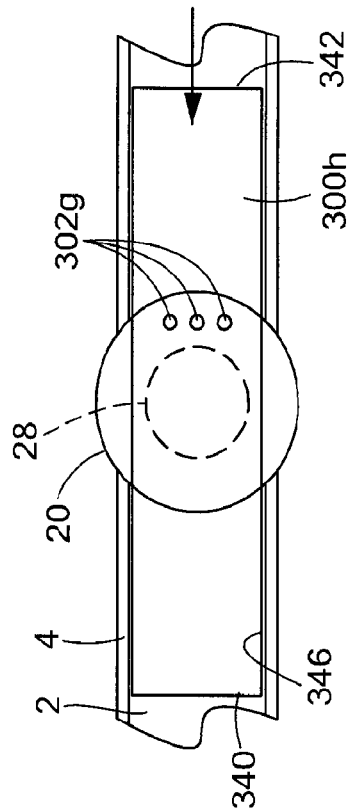
FIG. 15a is schematic side sectional view of another alternative embodiment stent disposed within a blood vessel having a side wall aneurysm.
Figure 15B:
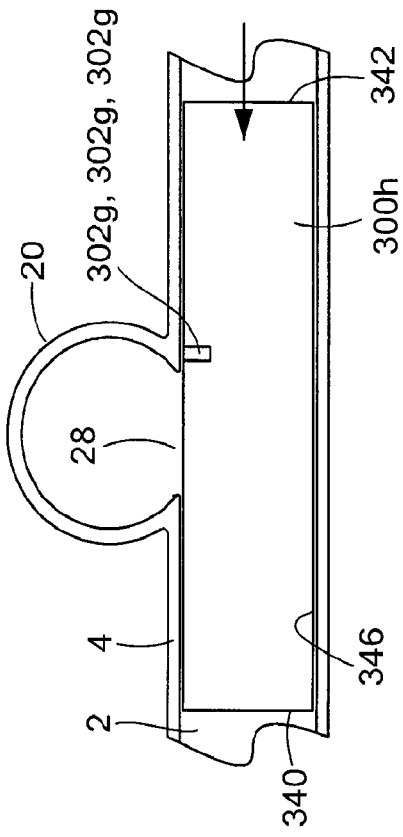

Referring to FIGS. 15a and 15b, a variation in vane configuration is illustrated with respect to a stent 300h that includes multiple rod-shaped vanes 302g. In this example, three vanes 302g are arranged in a spaced-apart relationship along a circumferential direction of the stent 300h.

Referring to FIGS. 16a and 16b, another variation in vane configuration is illustrated with respect to a stent 300i that includes two vanes 302g that are positioned upstream of the aneurysm opening 28 and are arranged in a spaced apart relationship along an axial direction of the stent 300i.

Referring to FIGS. 17a and 17b, another variation in vane configuration is illustrated with respect to a stent 300j that includes two vanes 302g1, 302g2. Like the preceding embodiment, the vanes 302g1, 302g2 are positioned upstream of the aneurysm opening 28 and are arranged in a spaced apart relationship along an axial direction of the stent 300i. However, in the stent 300j, the vanes 302g1, 302g2 are provided having the same shape but differing in size. For example, a first vane 302g1 is shorter than a second vane 302g2, and is positioned upstream relative to the second vane 302g2.

Figure 18A:
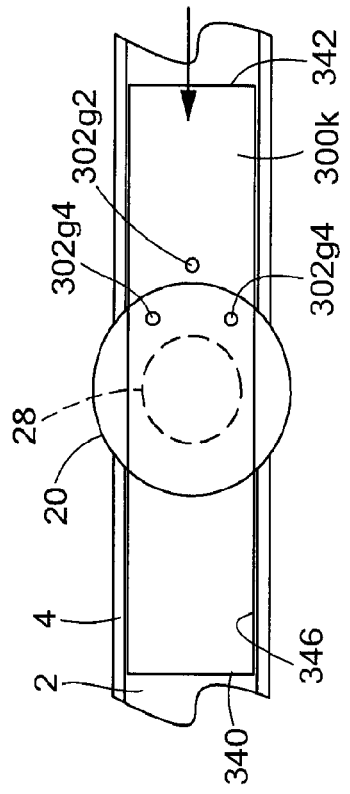
FIG. 18a is schematic side sectional view of another alternative embodiment stent disposed within a blood vessel having a side wall aneurysm.
Figure 18B:
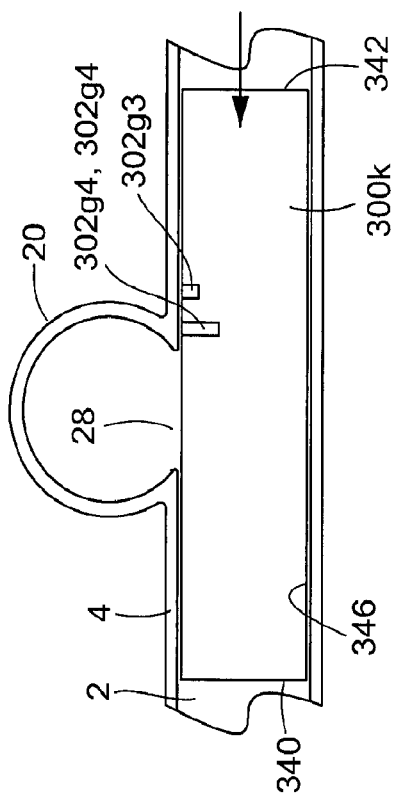

Referring to FIGS. 18a and 18b, another variation in vane configuration is illustrated with respect to a stent 300k that includes three vanes 302g3, 302g4, 302g4 are arranged within a stent 300k in a spaced apart relationship so as to form a V configuration. In this example, the vane 302g3 that is located relatively upstream and corresponds to the apex of the V is shorter than the vanes 302g4 that correspond to the legs of the V.

Figure 19A:
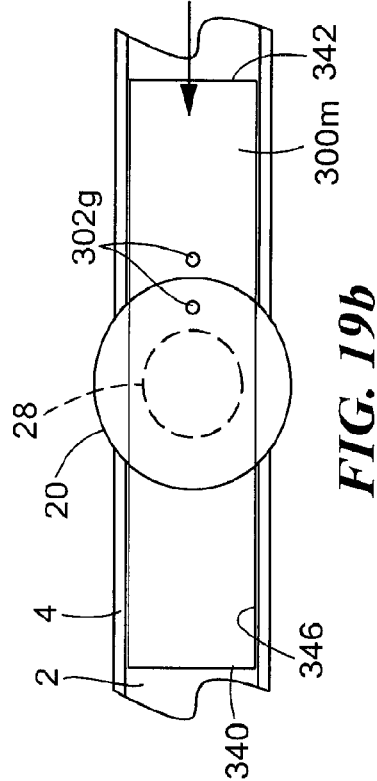
FIG. 19a is schematic side sectional view of another alternative embodiment stent disposed within a blood vessel having a side wall aneurysm.
Figure 19B:
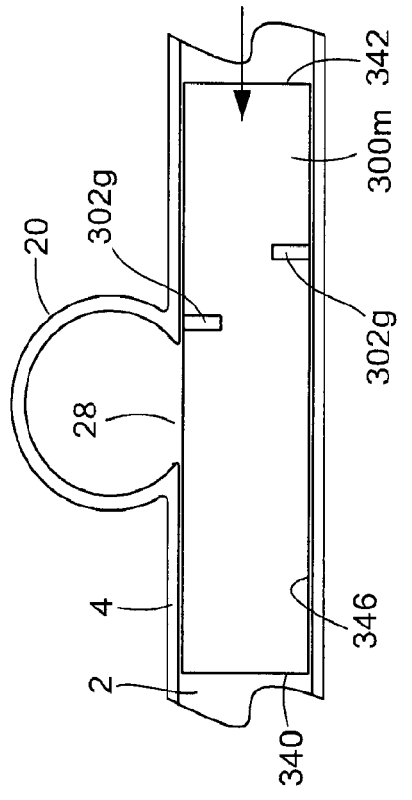

Referring to FIGS. 19a and 19b, another variation in vane configuration is illustrated with respect to a stent 300m that includes two vanes 302g, 302g. This embodiment illustrates that the position of the vanes 302g is not limited to a side of the stent 300m corresponding to the aneurysm 20. For example, two axially spaced vanes 302g, 302g having the same shape are provided on opposed sides of the stent 300m.

Although stent 300 is described here as having struts 348 that are arranged in an open cell structure, the stent 300 is not limited to this configuration. For example, in some embodiments the struts 348 may be arranged in a closed cell structure.

Figure 20:
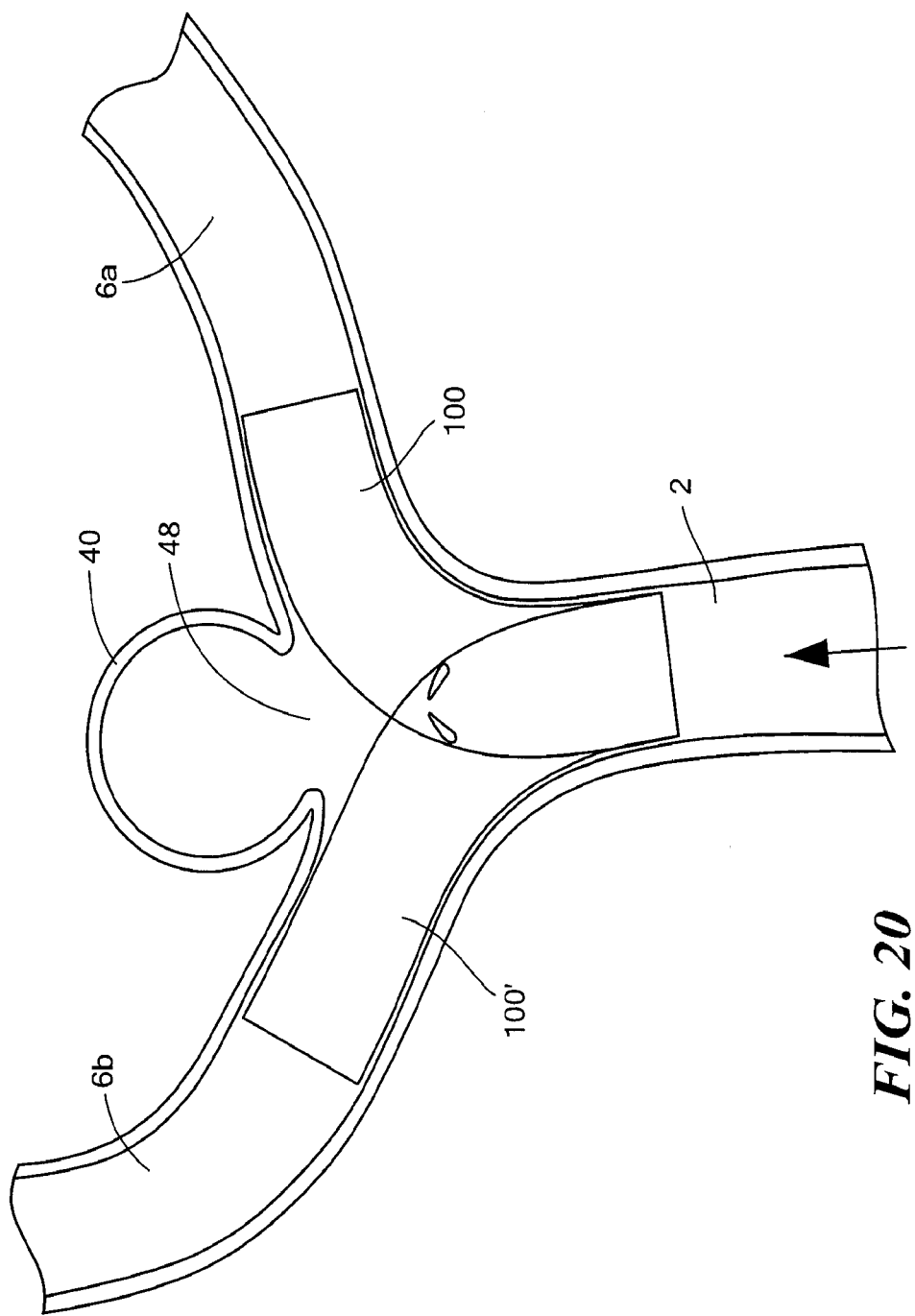
FIG. 20 is a schematic side sectional view of a pair of stents disposed within a blood vessel having a bifurcation aneurysm, each stent including a flow-shaping member.

Referring to FIG. 20, intracranial aneurysms are generally categorized into three types: a fusiform aneurysm in which the blood vessel wall forms a sausage like outward bulge about its entire circumference (not shown); a sidewall aneurysm 20 in which the blood vessel 2 forms an outward bulge from one portion of the sidewall 4 (FIG. 1); and a bifurcated aneurysm 40 in which the blood vessel 2 forms a bulge at an intersection of blood vessel branches 6 (FIG. 20). Although described herein with reference to treatment of a sidewall aneurysm 20, the stents 100, 200, 300 described here are not limited to use with a sidewall aneurysm 20, and can also be used with respect to a bifurcated aneurysm 40. For example, when treating a bifurcation aneurysm 40, two stents 100, 100' may be placed within the main vessel so that an end of one stent 100 extends into one vessel branch 6a, and an end of another stent 100' extends into the other vessel branch 6b. In this case, both of the stents 100, 100' extend across the aneurysm opening 48 and include flow-shaping members. The stents 100, 100' may be identical, respective mirror images, or unique.

EXAMPLE

The hemodynamic effects of placing a stent 100 including a helical coil wire flow disrupting strut 148 within a blood vessel 2 in the vicinity of an idealized side wall aneurysm 20 as shown in FIG. 2a have been analyzed using computational fluid dynamic techniques. Results of the analysis show that placement of a helical coil stent 100 as described results in a significant alteration of the flow within the aneurysm dome, and also leads to alterations in the downstream portion of the blood vessel 2, as discussed further below.

Figure 21:
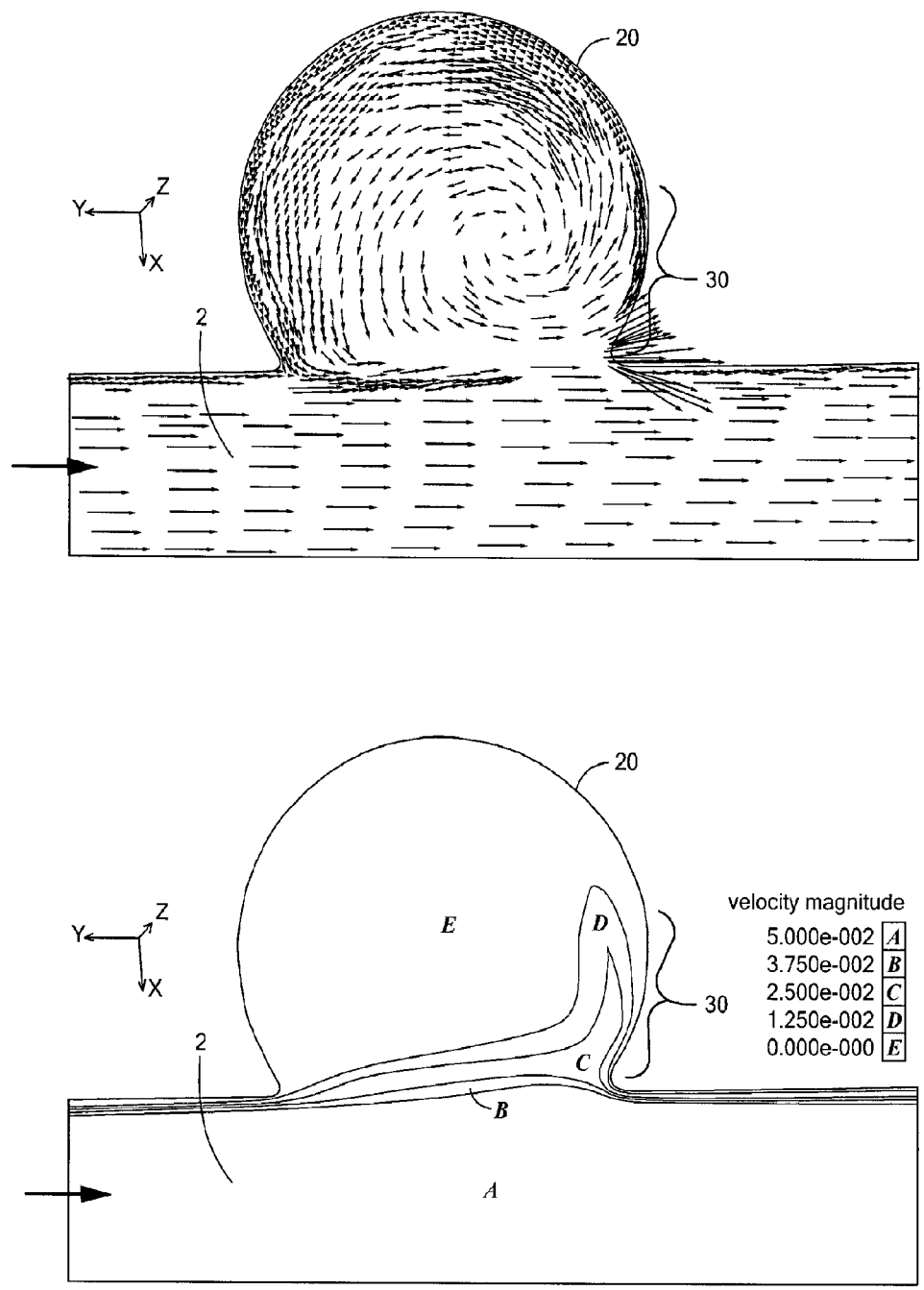
FIG. 21 is a side sectional view of a blood vessel including a sidewall aneurysm without a stent illustrating calculated blood flow direction (fine arrows) and velocity (labeled regions).

Referring to FIG. 21, fine arrows are used to indicate blood flow velocities and directions calculated for an unstented blood vessel 2 including the aneurysm 20. This figure illustrates vortex type swirling within the aneurysm 20 that is typical of an untreated aneurysm. Of particular note is the high velocities present at an inflow region 30 of the aneurysm 20 located adjacent the downstream side of the aneurysm opening 28, which are thought to contribute to aneurysm growth.

Figure 22:
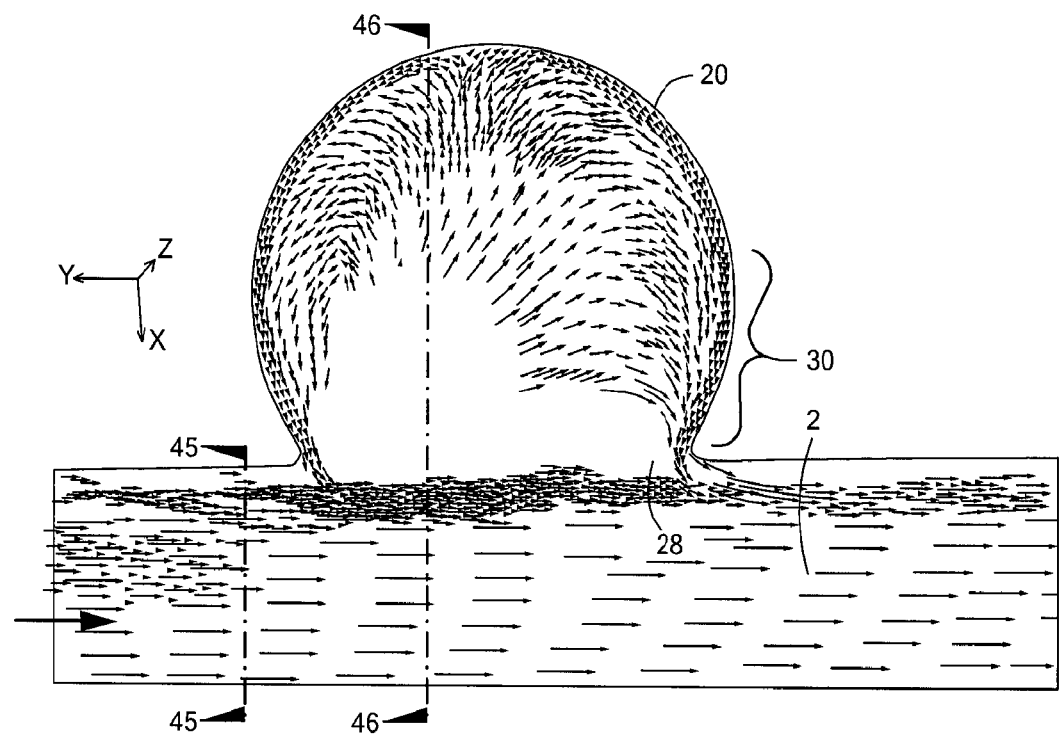
FIG. 22 is a side sectional view of the blood vessel of FIG. 21 including a sidewall aneurysm treated with the stent of FIG. 2a, illustrating calculated blood flow direction (fine arrows) and velocity (labeled regions).
Figure 22:
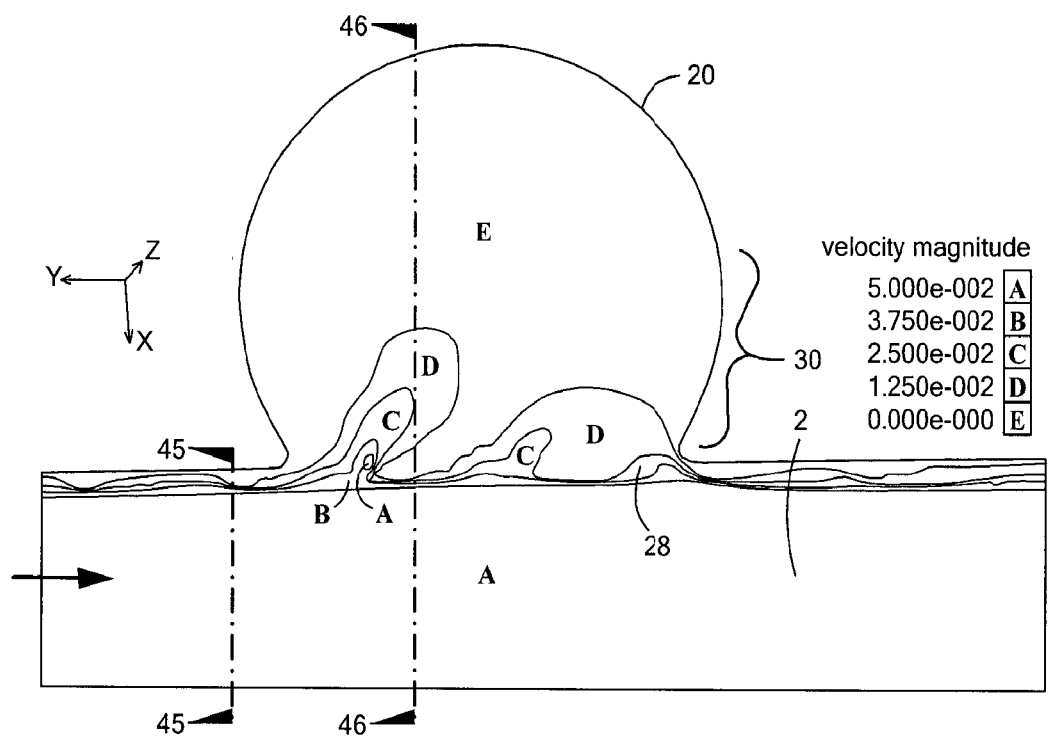

Referring to FIG. 22, when the blood vessel 2 including the aneurysm 20 is treated with a stent 100, the calculated blood flow velocities and directions are shown to be altered relative to the untreated vessel 2 shown in FIG. 43. In particular, the region of relatively high velocity is diverted away from the inflow region 30.

Figure 23:
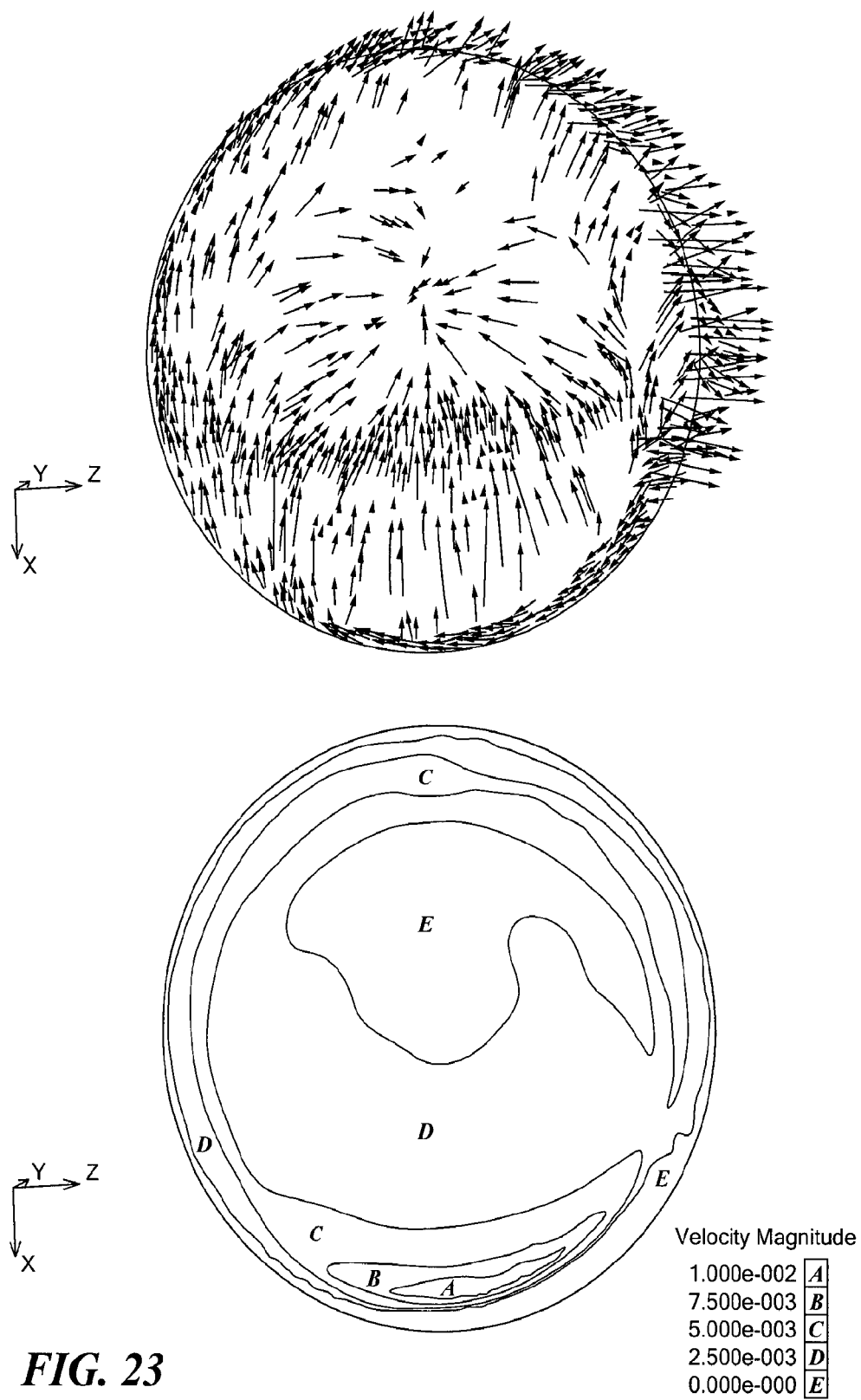
FIG. 23 is a transverse sectional view of the blood vessel of FIG. 22 as seen along line 45-45 illustrating calculated blood flow direction (fine arrows) and velocity (labeled regions).

Referring to FIG. 23, blood flow velocities and directions calculated for a cross section of the blood vessel upstream of the aneurysm are indicated by fine arrows. This figure illustrates that the helical stent 100 produces velocity components within the stent 100 that are directed both radially inward and circumferentially.

Figure 24:
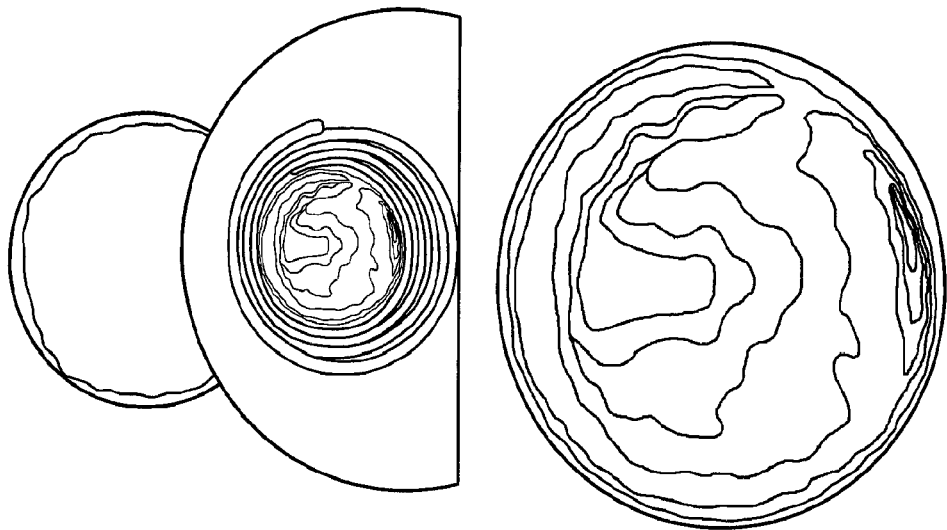
FIG. 24 are transverse sectional views of the blood vessel of FIG. 22 as seen along line 46-46 illustrating calculated blood flow direction (fine arrows) and velocity (labeled regions).
Figure 24:
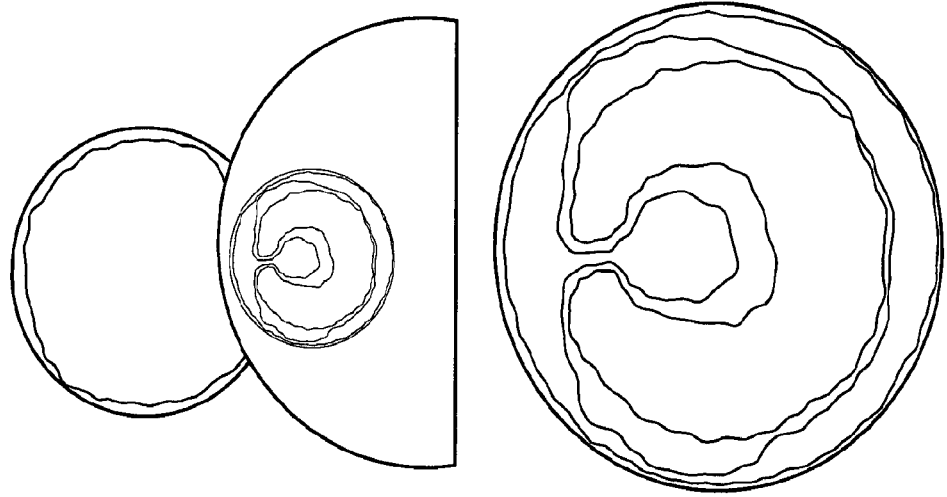

Referring to FIG. 24, blood flow velocities and directions calculated for a cross section of the blood vessel 2 corresponding to the aneurysm opening 28. This figure illustrates that the helical stent 100 produces velocity components within the stent 100 that are directed both circumferentially and radially inward away from the aneurysm.

Figure 25:
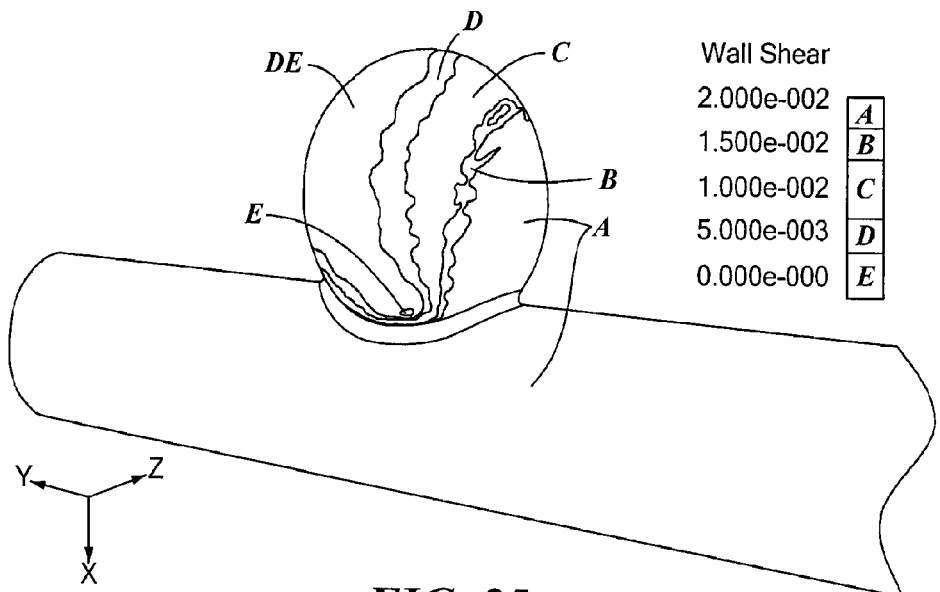
FIG. 25 is a perspective view of the blood vessel of FIG. 21 illustrating calculated wall shear stress for an untreated aneurysm.
Figure 26:
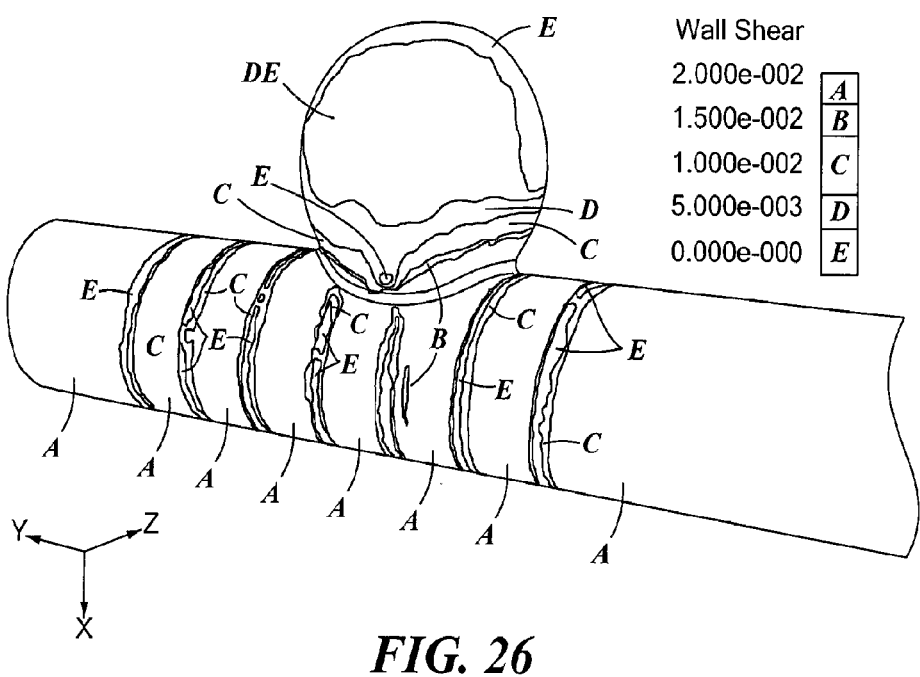

Referring to FIGS. 25 and 26, wall shear stresses calculated for the portion of the vessel including the aneurysm 20 are shown for a blood vessel 2 without a stent (FIG. 47) and a blood vessel 2 including a stent 100 (FIG. 48). Aneurysm inflow region wall shear stresses are clearly decreased for a blood vessel including the stent 100 relative to the untreated vessel 2.

A selected illustrative embodiment of the invention is described above in some detail. It should be understood that only structures considered necessary for clarifying the present invention have been described herein. Other conventional structures, and those of ancillary and auxiliary components of the system, are assumed to be known and understood by those skilled in the art. Moreover, while a working example of the present invention has been described above, the present invention is not limited to the working example described above, but various design alterations may be carried out without departing from the present invention as set forth in the claims.

What is claimed is:

1. An intravascular stent for treatment of an aneurysm in a vessel wall of a cranial blood vessel, the stent comprising a flow-shaping member including a flow-facing surface that protrudes from an inner surface of the stent and is configured to control at least one of the direction, velocity and secondary flow characteristics of the blood flow within the aneurysm, wherein the stent comprises a series of axially spaced-apart annular struts in which adjacent struts are joined by axially extending links, and the flow-shaping surface is provided by a surface of at least one strut.

2. An intravascular stent for treatment of an aneurysm in a vessel wall of a cranial blood vessel, the stent comprising a flow-shaping member including a flow-facing surface that protrudes from an inner surface of the stent and is configured to control at least one of the direction, velocity and secondary flow characteristics of the blood flow within the aneurysm, wherein the stent comprises a plurality of struts arranged to form a cylindrical body, and wherein the flow-shaping member comprises a vane protruding from an inner surface of the stent.

3. The stent of claim 2 wherein the stent is configured to be disposed in the vessel so that the flow-shaping member extends at least partially across the opening while permitting substantially unobstructed blood flow into the aneurysm.

4. The stent of claim 2 wherein the stent is configured to be disposed in the vessel so that the flow-shaping member is disposed in the vessel at a location upstream of the opening.

5. The stent of claim 2 wherein the flow-shaping member protrudes inward from the inner surface of the stent so that the flow-facing surface extends in a non-normal direction relative to the inner surface of the stent.

6. An intravascular stent for treatment of an aneurysm in a vessel wall of a cranial blood vessel, the stent comprising a flow-shaping member including a flow-facing surface that protrudes from an inner surface of the stent and is configured to control at least one of the direction, velocity and secondary flow characteristics of the blood flow within the aneurysm, wherein the flow-facing surface is disposed at an acute deflection angle that is measured relative to the inner surface of the stent.

7. The stent of claim 6 wherein the deflection angle is in the range of 2 degrees to 60 degrees.

8. The stent of claim 6 wherein the deflection angle is in the range of 3 degrees to 30 degrees.

9. The stent of claim 6 wherein the deflection angle is in the range of 4 degrees to 15 degrees.

10. The stent of claim 6 wherein the deflection angle of the flow-facing surface is configured to divert at least a portion of the blood flow toward an axial centerline of the stent.

11. The stent of claim 6 wherein the deflection angle of the flow-facing surface is configured to divert at least a portion of the blood flow in a direction tangential to an axial centerline of the stent.

12. The stent of claim 1 wherein the flow-shaping member has a generally elliptical cross section, the flow-shaping member being oriented so that the long axis of the elliptical cross section is angled relative to an inner surface of the stent.

13. The stent of claim 2 wherein the flow-shaping member has a generally rectangular cross section, the flow-shaping member being oriented so that the long axis of the rectangular cross section is angled relative to an inner surface of the stent.

14. The stent of claim 2 wherein the stent includes two vanes, the vanes being elongated and each including a first portion aligned with an axial direction of the vessel, and a second portion angled relative to the first portion.

15. The stent of claim 14 wherein the second portion extends in a circumferential direction of the stent.

16. The stent of claim 14 wherein the second portion extends in a radial direction of the stent.

17. The stent of claim 14 wherein the two vanes are arranged so that a second portion of the first strut is disposed within the opening, and the second portion of the second strut overlies the first portion of the first strut.

18. The stent of claim 14 wherein the two vanes are arranged so that the respective first portions are parallel to an axial direction of the strut, and the respective second portions are diverging.

19. The stent of claim 1 wherein the flow-facing surface of each annular strut is disposed at an acute deflection angle that is measured relative to the inner surface of the stent.

20. The stent of claim 19 wherein the deflection angle varies about a circumference of an annular strut.

21. The stent of claim 19 wherein a first portion of one of the annular struts has a first deflection angle, a second portion of the one of the annular struts has a second deflection angle, and the first deflection angle is different from the second deflection angle.

22. The stent of claim 21 wherein the first deflection angle is orthogonal to the second deflection angle.

23. The stent of claim 21 wherein the first deflection angle is an acute angle, and the second deflection angle is zero.

24. The stent of claim 21 wherein the first and second portions are diametrically opposed.

25. The stent of claim 1 wherein the flow-facing surface is configured to direct flow in a first direction, and the stent further comprises a second flow-shaping member including a second flow-facing surface configured to direct flow in a second direction that is different from the first direction.

26. The stent of claim 25 wherein the flow-shaping members have the same shape.

27. The stent of claim 25 wherein the flow-shaping members have different shapes.

28. The stent of claim 25 wherein the first direction is orthogonal to the second direction.

29. The stent of claim 25 wherein the first direction includes a flow-direction component in a first axial direction of the stent, and the second direction includes a flow-direction component in a direction opposed to the first axial direction of the stent.

30. The stent of claim 1 wherein the stent includes a strut having a generally elliptical cross section, the long axis of the elliptical cross section being angled relative to a longitudinal axis of the stent so that the strut protrudes into the flow, the strut extending axially along a helical path, the helical path having a helix angle of greater than 60 degrees.

31. The stent of claim 2 comprising a vane including a flow-facing surface that protrudes from an inner surface of the stent and is configured to disrupt laminar blood flow within the stent.

* * * * *